US012721819B2

(12) United States Patent
Harada et al.

(10) Patent No.: US 12,721,819 B2
(45) Date of Patent: Sep. 1, 2026

(54) LIPID PARTICLE

(71) Applicant: UNITED IMMUNITY, CO., LTD., Tokyo (JP)

(72) Inventors: Naozumi Harada, Tokyo (JP); Tadashi Inoue, Tokyo (JP); Takatoshi Soga, Tokyo (JP); Yuka Igarashi, Tokyo (JP)

(73) Assignee: UNITED IMMUNITY, CO., LTD., Tokyo (JP)

( * ) Notice: Subject to any disclaimer, the term of this patent is extended or adjusted under 35 U.S.C. 154(b) by 0 days.

(21) Appl. No.: 19/105,958

(22) PCT Filed: Mar. 14, 2024

(86) PCT No.: PCT/JP2024/009979
§ 371 (c)(1),
(2) Date: Feb. 24, 2025

(87) PCT Pub. No.: WO2024/190865
PCT Pub. Date: Sep. 19, 2024

(65) Prior Publication Data

US 2026/0000625 A1 Jan. 1, 2026

(30) Foreign Application Priority Data

Mar. 15, 2023 (JP) ................................ 2023-040536

(51) Int. Cl.
*A61K 9/51* (2006.01)
*A61K 39/00* (2006.01)

(52) U.S. Cl.
CPC ........ *A61K 9/5123* (2013.01); *A61K 39/0011* (2013.01); *A61K 2039/53* (2013.01); *A61K 2039/55555* (2013.01)

(58) Field of Classification Search
CPC ........... C12N 15/52; A61K 9/51; A61K 48/00
USPC ......................................................... 424/489
See application file for complete search history.

(56) References Cited

U.S. PATENT DOCUMENTS

| | | | |
|---|---|---|---|
| 4,636,381 | A | 1/1987 | Takada et al. |
| 8,058,069 | B2 | 11/2011 | Yaworski et al. |

FOREIGN PATENT DOCUMENTS

| | | |
|---|---|---|
| JP | 58-201711 | 11/1983 |
| JP | 2005-298644 | 10/2005 |
| JP | 2010-507421 | 3/2010 |
| JP | 2010-540498 | 12/2010 |
| JP | 2012-529464 | 11/2012 |
| WO | 2008/049633 | 5/2008 |
| WO | 2009/040426 | 4/2009 |
| WO | 2010/142685 | 12/2010 |

OTHER PUBLICATIONS

Albertsen et al., "The role of lipid components in lipid nanoparticles for vaccines and gene therapy." Advanced Drug Delivery Reviews 188 (2022) 114416. Available online Jul. 3, 2022 (Year: 2022).*
Lila et al., "Use of polyglycerol (PG), instead of polyethylene glycol (PEG), prevents induction of the accelerated blood clearance phenomenon against long-curculating liposomes upon repeated administration." International Journal of Pharmaceutics 456 (2013) 235-242. (Year: 2013).*
Kondo et al., "DNA separation by cholesterol-bearing pullan nanogels." Biomicrofluidics 4, 032210 (2010); doi: 10.1063/1.3479997. (Year: 2010).*
Tnchov et al., "Lipid Nanoparticles—From Liposomes to mRNA Vaccine Delivery, a Landscape of Research Diversity and Advancement" ASCNANO published Aug. 2021; https://doi.org/10.1021/acsnano.1c04996 (Year: 2021).*
Extended European Search Report issued Sep. 24, 2025 in European Patent Application No. 24770968.6.
Xiaojun Tao, et al., "Cholesterol-Modified Amino-Pullulan Nanoparticles as a Drug Carrier: Comparative Study of Cholesterol-Modified Carboxyethyl Pullulan and Pullulan Nanoparticles", Nanomaterials, 2016, vol. 6, No. 9, p. 165.
International Search Report issued Jun. 4, 2024 in International (PCT) Application No. PCT/JP2024/009979.
Notice of Reasons for Refusal issued Jun. 4, 2024 in Japanese Application No. 2024-517587 (with machine translation).
Mizuta et al., "Reversible conjugation of biomembrane vesicles with magnetic nanoparticles using a self-assembled nanogel interface: single particle analysis using imaging flow cytometry", Nanoscale Advances, 2022, vol. 4, No. 8, pp. 1999-2010.

* cited by examiner

*Primary Examiner* — Walter E Webb
(74) *Attorney, Agent, or Firm* — Wenderoth, Lind & Ponack, L.L.P.

(57) ABSTRACT

An object of the present invention is to provide a lipid particle that can be produced without using a PEG-modified lipid, or that exhibits higher drug effects, safety, or stability than those of a lipid particle produced using a PEG-modified lipid; or that has immunokinetics different from those of a lipid particle produced using a PEG-modified lipid.

A lipid particle comprising an ionized lipid, a phospholipid, and a sterol as lipid components of the lipid particle, and a modified polysaccharide containing a hydrophobic group.

19 Claims, 3 Drawing Sheets

LIPID PARTICLE

TECHNICAL FIELD

The present invention relates to a lipid particle and the like.

BACKGROUND ART

Lipid nano particles (LNPs) can encapsulate various drug agents and are used as drug delivery carriers. The recent COVID-19 pandemic has led to the widespread use of LNP-based vaccines for the prevention of infectious diseases.

LNPs currently used in vaccines contain polyethylene glycol (PEG)-modified lipids in order to inhibit particle aggregation (Patent Literature 1). It is currently not possible to obtain an LNP without using a PEG-modified lipid. However, since PEG has allergenic properties and high contact frequency due to its presence in various products used on a daily basis or for medical purposes, there is concern about PEG-related anaphylactic reactions.

CITATION LIST

Patent Literature

PTL 1: Specification of U.S. Pat. No. 8,058,069

SUMMARY OF INVENTION

Technical Problem

An object of the present invention is to provide a lipid particle that can be produced without using a PEG-modified lipid, or that exhibits higher drug effects, safety, or stability than those of a lipid particle produced using a PEG-modified lipid, or that has immunokinetics different from those of a lipid particle produced using a PEG-modified lipid.

Solution to Problem

The present inventors conducted extensive research in light of the above problems and surprisingly found that the above problems can be solved by a lipid particle comprising an ionized lipid, a phospholipid, and a sterol as lipid components of the lipid particle, and a modified polysaccharide containing a hydrophobic group. Based on this finding, the present inventors conducted further research and accomplished the present invention. Specifically, the present invention comprises the following aspects.

Item 1. A lipid particle comprising an ionized lipid, a phospholipid, and a sterol as lipid components of the lipid particle, and a modified polysaccharide containing a hydrophobic group.

Item 2. The lipid particle according to Item 1, wherein the content of the ionized lipid is 35 to 70 mol % based on 100 mol % of the lipid components of the lipid particle, the content of the phospholipid is 4 to 25 mol % based on 100 mol % of the lipid components of the lipid particle, and the content of the sterol is 15 to 55 mol % based on 100 mol % of the lipid components of the lipid particle.

Item 3. The lipid particle according to Item 1 or 2, wherein a polysaccharide that forms the modified polysaccharide comprises pullulan.

Item 4. The lipid particle according to any one of Items 1 to 3, wherein the hydrophobic group includes a hydrophobic group having a sterol skeleton.

Item 5. The lipid particle according to any one of Items 1 to 4, wherein the modified polysaccharide has a weight average molecular weight of 5000 to 2,000,000.

Item 6. The lipid particle according to any one of Items 1 to 5, comprising a drug agent.

Item 7. The lipid particle according to Item 6, wherein the drug agent is a nucleic acid.

Item 8. The lipid particle according to Item 7, wherein the nucleic acid is at least one member selected from the group consisting of mRNA, immunostimulatory double-stranded RNA, siRNA, miRNA, ribozyme, CpG oligo DNA, antisense oligo DNA, nucleic acid aptamer, decoy, double-stranded DNA for gene expression, and dinucleotide.

Item 9. The lipid particle according to Item 7 or 8, wherein the nucleic acid is mRNA or CpG oligo DNA.

Item 10. The lipid particle according to any one of Items 7 to 9, wherein the nucleic acid is mRNA.

Item 11. The lipid particle according to any one of Items 7 to 9, wherein the nucleic acid is CpG oligo DNA.

Item 12. The lipid particle according to any one of Items 1 to 11, wherein the ionized lipid is at least one member selected from the group consisting of amino lipids represented by formula (1):

(1)

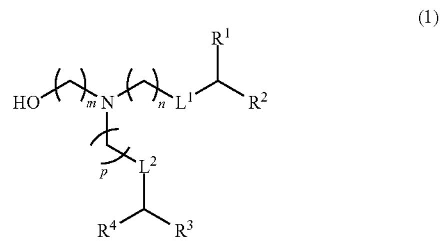

wherein $R^1$ represents an alkyl group, $R^2$ represents an alkyl group, $R^3$ represents an alkyl group, $R^4$ represents an alkyl group or a hydrogen atom, $L^1$ represents —O—C(═O)— or —C(═O)—O—, $L^2$ represents —O—C(═O)— or —C(═O)—O—, m represents an integer of 1 to 8, n represents an integer of 3 to 10, and p represents an integer of 3 to 10;

amino lipids represented by formula (2):

(2)

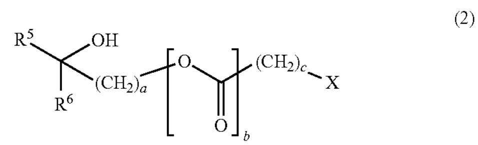

wherein a represents an integer of 3 to 5, b represents 0 or 1, c represents an integer of 0 to 4, $R^5$ and $R^6$ are the same or different and represent an alkyl group or an alkenyl group, and X represents an optionally substituted non-aromatic nitrogen-containing heterocyclic group or an optionally substituted amino group;

and amino lipids represented by formula (3):

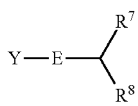

(3)

wherein $R^7$ and $R^8$ are the same or different and represent an alkyl group or an alkenyl group, Y represents an optionally substituted non-aromatic nitrogen-containing heterocyclic group or an optionally substituted amino group, and E represents a linker.

Item 13. The particle according to Item 1, further comprising a complex lipid that inhibits particle aggregation.

Item 14. The lipid particle according to any one of Items 1 to 13, wherein the content of the complex lipid is 0 to 2 mol % based on 100 mol % of the lipid components of the lipid particle.

Item 15. The lipid particle according to Item 13 or 14, wherein the complex lipid is a polyethylene glycol-lipid conjugate.

Item 16. The lipid particle according to any one of Items 1 to 15, wherein the mass average particle size is 10 to 200 nm.

Item 17. A medicine comprising the lipid particle according to any one of Items 1 to 16.

Item 18. The medicine according to Item 17, which is a therapeutic drug for cancers, immune disorders, central nervous system diseases, etc., an infectious disease vaccine, or a cancer vaccine.

Item 18A. A method for preventing or treating a cancer, an immune disorder, a central nervous system disease, or an infectious disease, the method comprising administering the lipid particle of any one of Items 1 to 16 to a subject (e.g., a patient) (preferably a subject with a cancer, a subject with an immune disease, a subject with a central nervous system disease, a subject with an infectious disease, or a subject in need of cancer prevention, a subject in need of immune disorder prevention, a subject in need of central nervous system disease prevention, or a subject in need of infectious disease prevention).

Item 18B. The lipid particle according to any one of Items 1 to 16, which is for use as a therapeutic agent for cancers, immune disorders, central nervous system diseases, or the like, or as an infectious disease vaccine or a cancer vaccine.

Item 18C. Use of the lipid particle of any one of Items 1 to 16 in production of a therapeutic agent for cancers, immune disorders, central nervous system diseases, or the like, or in production of an infectious disease vaccine or a cancer vaccine.

Item 18D. Use of the lipid particle of any one of Items 1 to 16 as a therapeutic agent for cancers, immune disorders, central nervous system diseases, or the like, or as an infectious disease vaccine or a cancer vaccine.

Item 19. The medicine according to Item 17 or 18, which is for use in subcutaneous, transvenous, intramuscular, intranasal, or intra-airway administration.

Advantageous Effects of Invention

The present invention can provide a lipid particle that can be produced without using a PEG-modified lipid; or that exhibits higher drug effects, safety, or stability than those of the lipid particle produced using a PEG-modified lipid; or that has immunokinetics different from those of a lipid particle produced using a PEG-modified lipid.

BRIEF DESCRIPTION OF DRAWINGS

FIG. 1 shows the results of the addition of LNP (EGFP) (Reference Example 2) or CHP:LNP (EGFP) (Example 2), and the results without the addition of LNP as a negative control. M0 indicates the results with M0 macrophages and M2 indicates results with M2-like macrophages.

DESCRIPTION OF EMBODIMENTS

Figure 1:
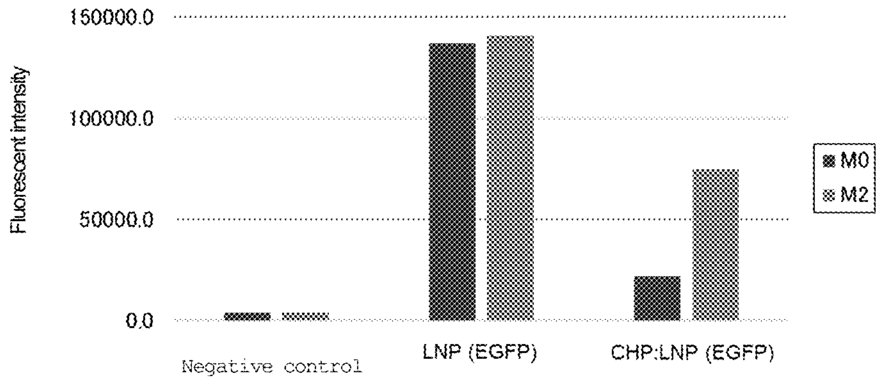
FIG. 1 shows the results of Test Example 5 in which after the addition of LNP, incubation was performed at 37° C. overnight without conducting treatment at 4° C. Specifically.

In the present specification, the terms "comprise" and "contain" include the concepts of "comprising," "containing," "essentially consisting of," and "consisting of."

1. Lipid Particle

In an embodiment, the present invention relates to a lipid particle comprising an ionized lipid, a phospholipid, and a sterol as lipid components of the lipid particle, and a modified polysaccharide containing a hydrophobic group (sometimes referred to as the "lipid particle of the present invention" in the present specification.) The lipid particle is explained below.

The ionized lipid is not particularly limited as long as it can form the lipid particle and exhibit a positive charge within the lipid particle. Examples of the ionized lipid include [4-hydroxybutyl)azanediyl]di(hexane-6,1-diyl)bis (2-hexyldecanoate) (ALC-0315), 9-heptadecanyl 8-{(2-hydroxyethyl) [6-oxo-6-(undecyloxy)hexyl]amino}octanoate (SM-102), (6Z,9Z,28Z,31Z)-heptatriaconta-6,9,28,31-tetraen-19-yl 4-(dimethylamino)butanoate (D-Lin-MC3-DMA), 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino)-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyloxy-3-(dimethylamino)acetoxypropane (DLin-DAC), 1,2-dilinoleyloxy-3-morpholino propane (DLin-MA), 1,2-dilinoloyl-3-dimethylamino propane (DLinDAP), 1,2-dilinoleylthio-3-dimethylamino propane (DLin-S-DMA), 1-linoleoyl-2-linoleoyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleoyloxy-N,N-dimethylaminopropane (DODMA), 1,2-distearyloxy-N,N-dimethylaminopropane (DSDMA), N-(1-(2,3-dioleoyloxy)propyl)-N,N,N-trimethylammonium chloride (DOTMA), N,N-distearyl-N,N-dimethylammonium bromide (DDAB), N-(1-(2,3-dioleoyloxy) propyl)-N, N, N-trimethylammonium chloride (DOTAP), 3-(N—(N', N'-dimethylaminoethane)-carbamoyl)cholesterol (DC-Chol), N-(1,2-dimyristyloxyprop-3-yl)-N, N-dimethyl-N-hydroxyethylammonium bromide (DMRIE), 2,3-dioleyloxy-N-[2 (spermine-carboxamide)ethyl]-N,N-dimethyl-1-propanaminium trifluoroacetate (DOSPA), dioctadecylamidoglycylspermine (DOGS), 3-dimethylamino-2-(cholesta-5-en-3-β-oxybutan-4-oxy)-1-(cis,cis-9,12-octadecadienoxy)propane (CLinDMA), 2-[5'-(cholesta-5-ene-3-β-oxy)-3'-oxapentoxy)-3-dimethyl-1-(cis, cis-9',1-2'-octadecadienoxy)propane (CpLinDMA), N,N-dimethyl-3,4-dioleyloxybenzylamine (DMOBA), 1,2-N,N'-diol- eylcarbamyl-3-dimethylaminopropane (DOcarbDAP), 1,2-N,N'-dilinoleylcarbamyl-3-dimethylaminopropane (DLincarbDAP), 1,1'-[7-[4-(dipropylamino)butyl]-7-hydroxy-1,13-tridecanediyl]di-(9Z)-9-octadecenoate (CL 4H6), 5-hydroxy-11-[[(9Z)-1-oxo-9-octadecen-1-yl]oxy]-5-[6[[(9Z)-1-oxo-9-octadecen-1-yl]oxy]hexyl]undecyl 1-methyl-4-piperidine carboxylate (CL 15H6), 1,1'-[7-[4-(dimethylamino) butyl]-7-hydroxy-1,13-tridecanediyl]di-(9Z)-9-octadecanate (CL 1H6), etc.

From the viewpoint of expression in the cell of the lipid particle according to the present invention, preferably from the viewpoint of expression in an antigen-presenting cell, the ionized lipid is at least one member selected from amino lipids represented by formula (1):

(1)

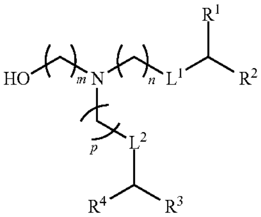

wherein $R^1$ represents an alkyl group, $R^2$ represents an alkyl group, $R^3$ represents an alkyl group, $R^4$ represents an alkyl group or a hydrogen atom, $L^1$ represents —O—C(═O)— or —C(═O)—O—, $L^2$ represents —O—C(═O)— or —C(═O)—O—, m represents an integer of 1 to 8, n represents an integer of 3 to 10, and p represents an integer of 3 to 10;

amino lipids represented by formula (2):

(2)

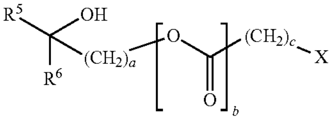

wherein a represents an integer of 3 to 5, b represents 0 or 1, c represents an integer of 0 to 4, $R^5$ and $R^6$ are the same or different and represent an alkyl group or an alkenyl group, and X represents an optionally substituted non-aromatic nitrogen-containing heterocyclic group or an optionally substituted amino group;

and amino lipids represented by formula (3):

(3)

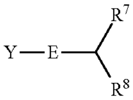

wherein $R^7$ and $R^8$ are the same or different and represent an alkyl group or an alkenyl group, Y represents an optionally substituted non-aromatic nitrogen-containing heterocyclic group or an optionally substituted amino group, and E represents a linker.

The use of such an amino lipid can more significantly exhibit the above accumulation properties.

The alkyl group and the alkenyl group are linear or branched, and particularly preferably linear. The lower limit of the number of carbon atoms in alkyl and alkenyl groups can be, for example, 1, 2, 3, 4, 5, 6, 7, 8, 9, or 10. The upper limit of the number of carbon atoms in alkyl and alkenyl groups can be, for example, 30, 25, 20, 18, 16, 15, 14, 13, 12, 11, 10, 9, 8, 7, 6, 5, or 4. The number of carbon atoms can be in a range of any combination of the above upper and lower limits.

The number of carbon atoms of the alkyl group represented by $R^1$ is not particularly limited as long as the compound of formula (1) is a lipid, and is, for example, 3 to 20. The number of carbon atoms is preferably 3 to 12, more preferably 3 to 10, even more preferably 4 to 8, still more preferably 5 to 7, and particularly preferably 6 from the viewpoint of accumulation properties.

The number of carbon atoms of the alkyl group represented by $R^2$ is not particularly limited as long as the compound of formula (1) is a lipid, and is, for example, 3 to 20. The number of carbon atoms is preferably 4 to 15, more preferably 5 to 12, even more preferably 6 to 10, still more preferably 7 to 9, and particularly preferably 8 from the viewpoint of accumulation properties.

The number of carbon atoms of the alkyl group represented by $R^3$ is not particularly limited as long as the compound of formula (1) is a lipid, and is, for example, 3 to 20. The number of carbon atoms is preferably 3 to 12, more preferably 3 to 10, even more preferably 4 to 8, still more preferably 5 to 7, and particularly preferably 6 from the viewpoint of accumulation properties.

$R^4$ is preferably an alkyl group from the viewpoint of accumulation properties.

The number of carbon atoms of the alkyl group represented by $R^4$ is not particularly limited as long as the compound of formula (1) is a lipid, and is, for example, 3 to 20. The number of carbon atoms is preferably 4 to 15, more preferably 5 to 12, even more preferably 6 to 10, still more preferably 7 to 9, and particularly preferably 8 from the viewpoint of accumulation properties.

$L^1$ is preferably —O—C(═O)— (the —O— side of the divalent group indicates the hydroxyl group side in formula (1)) from the viewpoint of accumulation properties.

$L^2$ is preferably —O—C(═O)— (the —O— side of the divalent group indicates the hydroxyl group side in formula (1)) from the viewpoint of accumulation properties.

m is preferably 2 to 6, more preferably 3 to 5, and particularly preferably 4 from the viewpoint of accumulation properties.

n is preferably 4 to 8, more preferably 5 to 7, and particularly preferably 6 from the viewpoint of accumulation properties.

P is preferably 4 to 8, more preferably 5 to 7, and particularly preferably 6 from the viewpoint of accumulation properties.

The number of carbon atoms of the alkyl group represented by $R^5$ is not particularly limited as long as the compound of formula (2) is a lipid, and is, for example, 12 to 24.

The number of carbon atoms of the alkyl group represented by $R^6$ is not particularly limited as long as the compound of formula (2) is a lipid, and is, for example, 12 to 24.

The number of carbon atoms of the alkyl group represented by $R^7$ is not particularly limited as long as the compound of formula (2) is a lipid, and is, for example, 12 to 24.

The number of carbon atoms of the alkyl group represented by $R^8$ is not particularly limited as long as the compound of formula (2) is a lipid, and is, for example, 12 to 24.

If the non-aromatic nitrogen-containing heterocyclic group and the amino group are substituted, the substituent is preferably an alkyl group. The alkyl group is, for example, an alkyl group having a number of carbon atoms of 1 to 4.

The non-aromatic nitrogen-containing heterocyclic group is a monovalent group obtained by removing one hydrogen atom from a non-aromatic nitrogen-containing heterocyclic ring. Examples of the non-aromatic nitrogen-containing heterocyclic ring include pyrrolidinyl, piperidinyl, morpholinyl, and piperazinyl groups.

The linker represented by E may be a linker with a number of chain constituent atoms of, for example, 1 to 10, and preferably 3 to 8. The linker is preferably an alkyl group that may comprise —O—C(═O)— or —C(═O)—O— in the chain.

The ionic lipids can be used alone or in a combination of two or more.

The content of the ionic lipid is preferably 35 to 70 mol %, more preferably 40 to 65 mol %, even more preferably 45 to 60 mol %, and still more preferably 45 to 55 mol % based on 100 mol % of the lipid components of the lipid particle from the viewpoint of lipid particle formation properties, accumulation properties, stability, etc.

The ionic lipid can be prepared by purchasing a commercially available product, or can be produced by or according to a known method. WO2018/230710 and WO2010/129687 can be referenced for production.

The phospholipid is not particularly limited as long as it can form the lipid particle. Examples include phosphatidylcholine, phosphatidylethanolamine, phosphatidylserine, phosphatidylinositol, phosphatidic acid, lysophosphatidylcholine, and lysophosphatidylethanolamine. Specific examples include distearoyl phosphatidylcholine (DSPC), dipalmitoyl phosphatidylcholine (DPPC), dioleoyl phosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), and egg phosphatidylcholine (EPC).

The phospholipid is preferably phosphatidylcholine, more preferably DSPC, DPPC, etc., and even more preferably DSPC from the viewpoint of lipid particle formation properties, stability, etc.

The phospholipids can be used alone or in a combination of two or more.

The content of the phospholipid is preferably 4 to 25 mol %, more preferably 4 to 20 mol %, even more preferably 4 to 15 mol %, still more preferably 6 to 12 mol %, and particularly preferably 8 to 11 mol % based on 100 mol % of the lipid components of the lipid particle from the viewpoint of lipid particle formation properties, stability, etc.

The sterol is not particularly limited as long as it has a sterol skeleton and can form the lipid particle. Examples of the sterol include cholesterol, cholesteryl hemisuccinate, lanosterol, dihydrolanosterol, desmosterol, dihydrocholesterol, phytosterol, phytosterol, stigmasterol, zymosterol, ergosterol, sitosterol, campesterol, brassicasterol, etc. In addition to these, examples include derivatives of cholesterol, such as cholestanol, cholestanone, cholestenone, coprostanol, cholesteryl-2'-hydroxyethyl ether, and cholesteryl-4'-hydroxybutyl ether.

The sterol is preferably cholesterol from the viewpoint of lipid particle formation properties, stability, etc.

The sterols can be used alone or in a combination of two or more.

The sterol content is preferably 15 to 55 mol %, more preferably 25 to 50 mol %, even more preferably 30 to 45 mol %, and still more preferably 35 to 45 mol % based on 100 mol % of the lipid components of the lipid particle from the viewpoint of lipid particle formation properties, stability, etc.

The modified polysaccharide is a compound obtained by modifying a polysaccharide, and is not particularly limited as long as it contains a hydrophobic group as a modifying group. In the present invention, it was found that a modified polysaccharide can be used to form a lipid particle (particularly, a lipid particle containing the lipids in the contents shown above) without using a PEG-modified lipid (it is preferable that a PEG-modified lipid is not used; however, a lipid particle may contain a PEG to a certain degree as long as PEG-related side reactions or the like can be avoided).

The polysaccharide that forms the modified polysaccharide (i.e., polysaccharide before modification) is not particularly limited as long as it is a polymer to which a sugar residue is glycosidically linked. Usable examples of sugar residues that form the polysaccharide include residues derived from sugars, such as monosaccharides (e.g., glucose, mannose, galactose, and fucose), disaccharides, or oligosaccharides. The sugar residue may be 1,2-, 1,3-, 1,4-, or 1,6-glycosidically linked, and the linkage thereof may be either an α- or β-linkage. Further, the polysaccharide may be linear or branched. Preferable sugar residues are glucose residues. Preferable polysaccharides are, for example, naturally occurring or synthetic pullulan, mannan, dextran, amylose, amylopectin, and the like. Of these, from the viewpoint of lipid particle formation properties, stability, etc., pullulan, mannan, dextran, and the like are preferably used; pullulan, mannan, and the like are more preferably used; and pullulan and the like are particularly preferably used.

The weight average molecular weight of the polysaccharide is not particularly limited as long as the modified polysaccharide can form a gelled particle, and is, for example, 5,000 to 2,000,000. The weight average molecular weight of the polysaccharide is preferably 10,000 to 1,000,000, more preferably 20,000 to 500,000, even more preferably 40,000 to 250,000, and still more preferably 80,000 to 125,000.

The polysaccharide used can be a commercially available product or a product obtained according to a known production method.

The hydrophobic group is not particularly limited as long as it is a group with hydrophobicity. From the viewpoint of lipid particle formation properties, stability, etc., the hydrophobic group is preferably a hydrophobic group having a sterol skeleton, a hydrocarbon group, or the like; and particularly preferably a hydrophobic group having a sterol skeleton The sterol skeleton is an alcohol in which a hydroxyl group is attached to a cyclopentahydrophenanthrene ring shown in formula (I). Symbols A to D in formula (I) represent each ring that forms the cyclopentahydrophenanthrene ring.

(I)

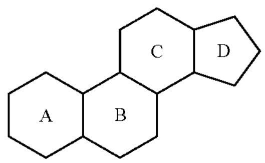

In the sterol skeleton, the cyclopentahydrophenanthrene ring may have a double bond, and the bonding position of the hydroxyl group is not particularly limited. Preferable are either sterols with a hydroxyl group at the C-3 position and a double bond in the B ring, or stanols with a hydroxyl group at the C-3 position and a saturated ring. Examples of the hydrophobic group having a sterol skeleton include groups derived from compounds with a modified sterol skeleton, for example, the ring-forming carbon is replaced by a hydrocarbon group (e.g., a $C_{1-20}$ linear or branched alkyl group). The phrase "group derived from" refers to a group of a compound from which a hydrogen atom or a functional group, such as a hydroxyl group, is removed.

Examples of the hydrophobic group having a sterol skeleton include cholesterol-derived groups, cholestanol-derived groups, lanosterol-derived groups, ergosterol-derived groups, R-sitosterol-derived groups, campesterol-derived groups, stigmasterol-derived groups, brassicasterol-derived groups, etc. Preferred among these are sterol-derived groups, such as cholesterol-derived groups, cholestanol-derived groups, lanosterol-derived groups, and ergosterol-derived groups; and more preferred are cholesterol-derived groups.

The hydrocarbon group as the hydrophobic group is not particularly limited, and examples include $C_{8-50}$ (preferably $C_{10-30}$, more preferably $C_{12-20}$) chain (preferably linear) hydrocarbon groups (preferably alkyl groups).

The weight average molecular weight of the modified polysaccharide is not particularly limited as long as the modified polysaccharide can form a gelled particle, and is, for example, 5,000 to 2,000,000. The weight average molecular weight of the modified polysaccharide is preferably 10,000 to 1,000,000, more preferably 20,000 to 500,000, even more preferably 40,000 to 250,000, and still more preferably 80,000 to 125,000.

The number of hydrophobic groups contained in the modified polysaccharide is not particularly limited as long as the modified polysaccharide can form a gelled particle. The number of hydrophobic groups is, for example, 1 to 10, and preferably 1 to 5, per 100 sugar residues that form the polysaccharide.

The hydrophobic group can be linked to the polysaccharide directly or indirectly (e.g. through a linker).

The modified polysaccharide is preferably, for example, one containing 1 to 10 (preferably 1 to 5) sugar units per 100 sugar residues that form the polysaccharide, whose primary hydroxyl group is represented by formula (II): $—O—(CH_2)_xCONH(CH_2)_yNH—CO—O—R$ (II), wherein R is a hydrophobic group having a sterol skeleton or a hydrocarbon group, x is 0 or 1, and y is any positive integer. y is preferably 1 to 8.

The modified polysaccharide can be synthesized by or according to a known method (e.g., WO00/12564). For example, the following method can be used. First, $C_{12-50}$ hydroxyl group-containing hydrocarbon or sterol, and a diisocyanate compound represented by formula $OCN—R^ANCO$, wherein $R^A$ is $C_{1-50}$ hydrocarbon group, are reacted to produce an isocyanato group-containing hydrophobic compound in which one molecule of $C_{12-50}$ hydroxyl group-containing hydrocarbon or sterol is reacted. Then, the resulting isocyanato group-containing hydrophobic compound and a polysaccharide are further reacted to produce a hydrophobic group-containing polysaccharide containing a $C_{12-50}$ hydrocarbon group or a stearyl group as a hydrophobic group. The obtained reaction product is purified with a ketone solvent, whereby a high-purity hydrophobic group-containing polysaccharide can be produced.

The modified polysaccharides can be used alone or in a combination of two or more.

From the viewpoint of lipid particle formation properties, stability, etc., the content of the modified polysaccharide is, for example, 0.5 to 15 mol %, and preferably 1 to 10 mol % based on 100 mol % of the lipid components of the lipid particle.

The lipid particle of the present invention can contain a complex lipid that inhibits particle aggregation (hereinafter simply referred to as "complex lipid"). The complex lipid is not particularly limited as long as it can inhibit the aggregation of the lipid particle and can form the lipid particle. Examples include polyethylene glycol (PEG)-lipid conjugates, polyamide (*ATTA*)-lipid conjugates, cationic polymer-lipid conjugates (CPL), etc. Specific examples include PEG-lipids, including PEG-diacylglycerol (DAG), PEG-dialkyloxypropyl (DAA), PEG-phospholipids, PEG-ceramides (Cer), or mixtures thereof. The molecular weight of the PEG portion of the PEG-lipid conjugate is not particularly limited, and is, for example, 200 to 10000, preferably 500 to 7000, more preferably 500 to 4000, even more preferably 1000 to 3000, and still more preferably 1500 to 2500.

The complex lipids can be used alone or in a combination of two or more.

The content of the complex lipid is, for example, 0 to 2 mol % based on 100 mol % of the lipid components of the lipid particle from the viewpoint of lipid particle formation properties, stability, avoiding anaphylactic shock, etc. The content of the complex lipid is preferably 0 to 1 mol %, more preferably 0 to 0.5 mol %, more preferably 0 to 0.2 mol %, even more preferably 0 to 0.1 mol %, still more preferably 0 to 0.01 mol %, and particularly preferably 0 mol % (without a complex lipid).

The lipid particle of the present invention preferably contains a drug agent. The drug agent is not particularly limited, and examples include a nucleic acid adjuvant and an anticancer agent, and a combination of these.

In one preferable embodiment of the present invention, the drug agent is placed inside (separated from the outside of the lipid particle) the lipid particle of the present invention. Preferably, the drug agent (particularly, a nucleic acid) is placed inside the lipid particle of the present invention in a state in which it is complexed with the ionized lipid.

The nucleic acid of the present invention is not particularly limited, and examples include mRNA, immunostimulatory double-stranded RNA (e.g. poly-IC RNA), siRNA, miRNA, ribozyme, CpG oligo DNA, antisense oligo DNA, nucleic acid aptamer, decoy, double-stranded DNA for gene expression, and dinucleotide. The nucleic acid includes not only DNA and RNA, but also other substances that can become pharmaceutical active ingredients. Examples also include known chemically modified DNA, RNA, and other substances listed below. To prevent degradation by hydrolases such as nucleases, the phosphate residue (phosphate) of each nucleotide can be substituted, for example, with a chemically modified phosphoric acid residue, such as phosphorothioate (PS), methyl phosphonate, or phosphorodithionate. The hydroxyl group at the 2-position of the sugar (ribose) of each ribonucleotide may be substituted with —OR (R represents, for example, $CH_3$ (2'-O-Me), $CH_2CH_2OCH_3$ (2'-O-MOE), $CH_2CH_2NHC(NH)NH_2$, $CH_2CONHCH_3$, $CH_2CH_2CN$, etc.). Additionally, the base moiety (pyrimidine, purine) can be chemically modified by, for example, introduction of a methyl group or a cationic functional group into the 5-position of the pyrimidine base, or substitution of the carbonyl group at the 2-position with thiocarbonyl. Additionally, examples of nucleic acid include, but are not limited to, those formed by modifying the phosphate moiety or the hydroxyl portion, for example, by biotin, an amino group, a lower alkyl amine group, or an acetyl group. The term "nucleic acid" also includes BNA (bridged nucleic acid, LNA (locked nucleic acid), and PNA (peptide nucleic acid).

The nucleic acid of the present invention can be preferably CpG oligo DNA or mRNA, and particularly mRNA encoding a microbial antigen or cancer antigen as described below.

Examples of CpG oligo DNA are as follows.

Class A: D35-CpG, ODN1585, ODN2216, ODN2336, etc.

Class B: K3-CpG, ODNBW006, ODND-SL01, ODN1668, OND1826, OND2006 (CpG7909, PF-3512676), ODN2007, ODN684, etc.

Class C: ODND-SL03, ODN 2395, ODN M362, etc.

Other examples include CpG-28, CpG-685 (GNKG-168), CpG-ODN C274, KSK-13 (KSK-CpG), CpG ODN 10104 (CpG-10104), CpG ODN-1585, ODN-5890, 1018-ISS, EMD-1201081 (HYB-2055, IMO-2055), etc.

As the CpG oligo DNA, commercially available products can be used, or those obtained according to a known production method can be used. For example, based on the contents of US 2022/0111061A1, it may be modified CpG oligo DNA containing a hydrophobic group A with a sterol skeleton, but is preferably unmodified CpG oligo DNA containing a hydrophobic group A with a sterol skeleton.

When the nucleic acid is mRNA, examples of the microbial antigen that the mRNA encodes include viral antigens, bacterial antigens, etc. Viral antigen-derived viruses are not particularly limited, and include influenza viruses (e.g. type A, B, etc.), rubella virus, Ebola virus, coronavirus, measles virus, varicella-zoster virus, herpes simplex virus, mumps virus, arbovirus, RS virus, SARS virus, hepatitis virus (for example, hepatitis B virus, hepatitis C virus, etc.), yellow fever virus, AIDS virus, rabies virus, hantavirus, dengue virus, Nipah virus, lyssavirus, and other enveloped viruses (viruses with envelopes); and non-enveloped viruses (viruses without envelopes) such as adenovirus, norovirus, rotavirus, human papillomavirus, poliovirus, enterovirus, coxsackievirus, human parvovirus, encephalomyocarditis virus, and rhinovirus. Bacterial antigen-derived bacteria are not particularly limited, and examples include *Bordetella pertussis, Tetanus bacillus, Corynebacterium diphtheriae, Salmonella enterica, Helicobacter pylori, Clostridium perfringens, Clostridium botulinum, Campylobacter, Escherichia coli, Staphylococcus aureus, Streptococcus pyogenes, B. cereus, Vibrio parahaemolyticus, Propionibacterium acnes, Enterococcus faecalis, Clostridium difficile, Streptococcus pneumoniae, Haemophilus influenzae, Moraxella pneumoniae, Klebsiella pneumoniae, Corynebacterium, Streptococcus, Pseudomonas aeruginosa, Staphylococcus, Mycoplasma, Candida* spp., and *Aspergillus* spp.

When the nucleic acid is mRNA, the cancer antigen that the mRNA encodes is not limited. The cancer antigen can be selected from ERK1, ERK2, MART-1/Melan-A, gp100, adenosine deaminase binding protein (ADAbp), FAP, cyclophilin b, colorectal-associated antigen (CRC)-C017-1A/GA733, carcinoembryonic antigen (CEA), CAP-1, CAP-2, etv6, AML1, prostate-specific antigen (PSA), PSA-1, PSA-2, PSA-3, prostate-specific membrane antigen (PSMA), T cell receptor/CD3-zeta chain, CD20, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5, GAGE-1, GAGE-2, GAGE-3, GAGE-4, GAGE-5, GAGE-6, GAGE-7, GAGE-8 and GAGE-9, BAGE, RAGE, LAGE-1, NAG, GnT-V, MUM-1, CDK4, tyrosinase, P53, MUC family, HER2/neu, p2iras, RCAS1, α-fetoprotein, E-cadherin, α-catenin, β-catenin, γ-catenin, p120ctn, gp100Pmel117, PRAME, NY-ESO-1, cdc27, adenomatous polyposis *coli* (APC) protein, fodrin, connexin 37, Ig idiotype, p15, gp75, GM2 ganglioside, GD2 ganglioside, human papillomavirus protein, smad family of tumour antigens, imp-1, PlA, EBNA (EBV nuclear antigen)-1, brain glycogen phosphorylase, SSX-1, SSX-2 (HOM-MEL-40), SSX-1, SSX-4, SSX-5, SCP-1, CT-7, CD20, c-erbB-2, and partial peptides thereof.

The target cancer is not particularly limited. Examples include leukemia (including chronic lymphocytic leukemia and acute lymphocytic leukemia), lymphoma (including non-Hodgkin lymphoma, Hodgkin lymphoma, T-cell lymphoma, B-cell lymphoma, Burkitt lymphoma, malignant lymphoma, diffuse lymphoma, and follicular lymphoma), myeloma (including multiple myeloma), breast cancer, colon cancer, kidney cancer, gastric cancer, ovarian cancer, pancreatic cancer, cervical cancer, endometrial cancer, esophageal cancer, liver cancer, head and neck squamous epithelial cancer, skin cancer, malignant melanoma, urinary tract cancer, prostate cancer, villous cancer, pharyngeal cancer, laryngeal cancer, thecoma, male germinoma, endometrial hyperplasia, endometriosis, embryoma, fibrosarcoma, Kaposi sarcoma, hemangioma, cavernous hemangioma, hemangioblastoma, retinoblastoma, astrocytoma, neurofibroma, oligodendroglioma, medulloblastoma, neuroblastoma, glioma, rhabdomyosarcoma, medulloblastoma, osteogenic sarcoma, leiomyosarcoma, thyroid sarcoma, Wilms tumor, and the like.

Examples of adjuvants are not particularly limited as long as they exhibit adjuvant functions of assisting or enhancing the original function of the active ingredient by the combination use with the active ingredient of the main agent. Specifically, the adjuvant is selected from nucleic acid, lipopolysaccharide, lipopeptide, synthetic low-molecular-weight compounds, etc., and is preferably CpG oligo DNA, poly IC RNA, imidazoquinoline (e.g., R848 or imiquimod), STING agonist (e.g., cyclic di-GMP), monophosphoryl lipid, lipopeptide, etc. In addition to the above, examples of the adjuvant include a taxane-based drug, an anthracycline-based drug, an inhibitor of JAK/STAT, an inhibitor of indole dioxygenase (IDO), an inhibitor of tryptophan dioxygenase (TDO), etc. These inhibitors include compounds having antagonistic action against the factor, as well as neutralizing antibodies of the factor, siRNA, and antisense DNA.

Examples of the anticancer agent include an alkylating agent, an antimetabolite, a microtubule inhibitor, an antibiotic anticancer agent, a topoisomerase inhibitor, a platinum preparation, a molecularly targeted drug, a hormonal agent, and a biological preparation.

The drug agents can be used alone or in a combination of two or more.

In the lipid particle of the present invention, the mass ratio of the drug agent to CHP, which is a lipid particle component (CHP/mRNA by mass) is 200 or less, more preferably 100 or less, and even more preferably 90 or less. The upper limit of the mass ratio can be, for example, 70, 50, 40, 30, 20, 10, or 8. The lower limit of the mass ratio can be, for example, 0.01, 0.02, 0.05, 0.1, 0.2, 0.5, or 1. The upper limit and the lower limit can be freely combined.

In one embodiment of the present invention, a liquid containing the lipid particle of the present invention can contain a drug agent (preferably nucleic acid, and more preferably mRNA), in a concentration of 1 to 1000 μg/mL, preferably 5 to 500 μg/mL, more preferably 15 to 400 μg/mL, even more preferably 30 to 300 μg/mL, and still more preferably 50 to 200 μg/mL.

The lipid particle of the present invention may contain other components (except for a solvent) in addition to the above components. Examples of other components include various components known to be incorporated into the lipid particle. Examples include an antioxidant and a membrane protein.

The antioxidant can be added to prevent oxidation of the membrane, and is optionally used as a component of a membrane. Examples of antioxidants used as a component of a membrane include butylated hydroxytoluene, propyl gallate, tocopherol, tocopherol acetate, mixed tocopherol concentrate, vitamin E, ascorbic acid, L-ascorbyl stearate, ascorbyl palmitate, sodium hydrogen sulfite, sodium sulfite, sodium edetate, erythorbic acid, and citric acid.

A membrane protein can be added to add functions to a membrane, or to stabilize the structure of a membrane, and is optionally used as a component of a membrane. Examples of membrane proteins include peripheral membrane proteins, integral membrane proteins, albumin, and recombinant albumins.

The other components are present in an amount of, for example, 10 mass % or less, preferably 5 mass % or less, more preferably 2 mass % or less, and still more preferably 1 mass % or less, based on 100 mass % of the lipid particle of the present invention.

The mass average particle size of the lipid particle of the present invention is, for example, 200 nm or less, preferably 10 to 200 nm, more preferably 20 to 200 nm, even more preferably 40 to 190 nm, still more preferably 40 to 180 nm, and particularly preferably 40 to 160 nm. The particle size can be measured by dynamic light scattering.

The lipid particle of the present invention is typically formed in an aqueous solution. Examples of the aqueous solution include various buffer solutions (e.g., acetate buffer, phosphate buffer, formate buffer, and histidine buffer).

The lipid particle of the present invention can be preferably produced by a method comprising a step (step 1) of either mixing an alcohol solution containing lipid components of the lipid particle and an aqueous solution containing a modified polysaccharide (and preferably further containing a drug agent) or mixing an alcohol solution containing lipid components of the lipid particle, an aqueous solution (preferably further containing a drug agent), and an aqueous solution containing a modified polysaccharide. This method ensures easy and efficient obtainment of the lipid particle of the present invention without using a PEG-modified lipid, or easy and efficient obtainment of the lipid particle of the present invention that can avoid PEG-related side reactions etc.

The alcohol as a solvent of the alcohol solution is not particularly limited as long as the alcohol can dissolve the lipid. A preferable alcohol is ethanol.

The alcohol solution preferably contains the lipid components of the lipid particle in the molar ratio described above. Thus, the lipid particle containing the lipid components of the lipid particle in the above molar ratio can be obtained.

The lipid concentration in the alcohol solution is, for example, 2 to 20 mM, and preferably 4 to 12 mM.

The aqueous solution is a solution of a solvent that contains water (the water content being preferably 80% or more, 90% or more, 95% or more, or 100%).

The concentration of the modified polysaccharide in the aqueous solution is, for example, 0.2 to 5 mg/mL, preferably 0.4 to 3 mg/mL, and more preferably 0.6 to 1.5 mg/mL.

The mixture ratio of the aqueous solution to the alcohol solution (the aqueous solution/the alcohol solution, v/v) is, for example, 1 to 20, and preferably 2 to 4.

Mixing is not particularly limited as long as the mixing mode allows the formation of the lipid particle. For example, the aqueous solution and the alcohol solution can be intensely stirred with a vortex mixer or the like. Alternatively, when mixing is performed using a reaction system with a microchannel, it is performed in a reaction system.

Step 1 can be performed, for example, at room temperature, or with heating.

The lipid particle of the present invention can be produced without using a PEG-modified lipid, and/or is useful in that it has higher drug effects, safety, or stability than those of a lipid particle produced using a PEG-modified lipid, or it exhibits immunokinetics different from those of a lipid particle produced using a PEG-modified lipid.

In another embodiment of the lipid particle of the present invention, a complex lipid that inhibits particle aggregation of a PEG-modified lipid etc. can be further included. This embodiment is effective in that it exhibits higher drug effects, safety, or stability than those of a lipid particle produced using a PEG-modified lipid; or that has immunokinetics different from those of a lipid particle produced using a PEG-modified lipid.

Safety can be, for example, reduced induction of anti-PEG antibody, reduced inflammation at the site of administration, reduced generation of heat after administration, etc.

Stability is the stability of the preparation. For example, an increase in particle size due to freezing and melting is suppressed. Specifically, the lipid particle containing a conventional PEG-modified lipid represented by the COVID-19 vaccine is unable to withstand freezing and melting, and repeated freezing and melting increases the particle size regardless of the presence or absence of an isotonifier (sucrose). Since the lipid particle of the present invention contains a modified polysaccharide such as CHP, the stability of the lipid particle preparation can be improved. The lipid particle of the present invention, which does not contain a PEG-modified lipid made by the production method of Example 4 (Method 2) below has increased stability for freezing and melting, and can suppress an increase in particle size even without sucrose.

Immunokinetics can be, for example, a difference in quality of induced cell immunity.

2. Use

The lipid particle of the present invention can contain a drug agent and has selective accumulation on DC-SIGN (CD209)-expressing cells (e.g., M2-like macrophages and antigen-presenting cells). Accordingly, the lipid particle of the present invention can be used as a medicine, reagent, etc. (also referred to as "the drug agent of the present invention" in the present specification), specifically used as a therapeutic drug for cancers, immune disorders, diabetes-induced diseases, central nervous system diseases, etc., or as an infectious disease vaccine or a cancer vaccine. The infectious disease vaccine is not particularly limited as long as it is used for infectious diseases, and includes vaccines for prevention as well as vaccines for treatment.

The drug agent of the present invention is not particularly limited as long as it comprises the lipid particle of the present invention. The drug agent of the present invention may further contain additives, if necessary. Examples of additives include bases, carriers, solvents, dispersants, emulsifiers, buffers, stabilizers, excipients, binders, disintegrators, lubricants, thickeners, moisturizers, coloring agents, flavoring agents, chelating agents, and the like.

The usage mode of the drug agent of the present invention is not particularly limited, and a suitable usage mode can be used depending on the type thereof. The drug agent of the present invention can be used, for example, in vitro (e.g., added to a medium of cultured cells) or in vivo (e.g., administered to an animal) depending on the use thereof.

The application object of the drug agent of the present invention is not particularly limited. Examples of mammals include humans, monkeys, mice, rats, dogs, cats, rabbits, pigs, horses, cows, sheep, goats, deer, and the like. Further, examples of cells include animal cells and the like. The type of cell is also not particularly limited, and examples include blood cells, hematopoietic stem cells/progenitor cells, gametes (sperm and egg), fibroblasts, epithelial cells, vascular endothelial cells, neurons, hepatocytes, keratinocytes, muscle cells, epidermal cells, endocrine cells, ES cells, iPS cells, tissue stem cells, cancer cells, and the like.

The drug agent of the present invention can have any dosage form, and examples include oral dosage forms, such as tablets (including orally disintegrating tablets, chewable tablets, foaming tablets, troches, jelly drops, etc.), pills, granules, subtle granules, powders, hard capsules, soft capsules, dry syrups, liquids (including drinkable preparations, suspensions, and syrups), and jellies; and parenteral dosage forms, such as injectable preparations (e.g., drip injections (intravenous drip injections etc.), intravenous injections, intramuscular injections, subcutaneous injections, and intradermal injections), external preparations (e.g., ointments, poultices, and lotions), suppositories, inhalants, eye drops, eye ointments, nasal drops, ear drops, and liposome preparations.

The route of administration of the drug agent of the present invention is not particularly limited as long as the desired effects are obtained. Examples include oral administration; enteral administration, such as tube feeding and enema administration; parenteral administration, such as intravenous administration, intraarterial administration, intramuscular administration, intracardiac administration, subcutaneous administration, intradermal administration, intraperitoneal administration, intranasal administration, intra-airway administration, instillation administration; and the like.

The content of the lipid particle of the present invention in the drug agent of the present invention varies depending on the usage mode, application object, the state of the applied object, etc., and is not limited. For example, the content of the lipid particle is 0.0001 to 100 wt %, and is preferably 0.001 to 50 wt %.

The dose of the drug agent of the present invention when administered to an animal is not particularly limited as long as it is an effective amount for expressing drug effects. In the case of oral administration, the weight of the lipid particle of the present invention is generally 0.1 to 1000 mg/kg body weight per day, and preferably 0.5 to 500 mg/kg body weight per day. In the case of parenteral administration, the weight of the lipid particle of the present invention is 0.01 to 100 mg/kg body weight per day, and preferably 0.05 to 50 mg/kg body weight per day. The above dose can be suitably increased or decreased according to the age, pathological conditions, symptoms, etc.

EXAMPLES

The present invention is described in detail below based on Examples; however, the present invention is not limited to these Examples.

Preparation Example 1. Preparation of Pullulan Nanogel

According to a previously reported document (Macromolecules 1993, 23, 3062-3068), cholesterol-modified pullulan (CHP) in which 1.2 cholesterols per 100 monosaccharides were introduced into pullulan having a weight average molecular weight of 100,000 was produced. Using the produced CHP, a pullulan nanogel solution was prepared according to a known method.

Reference Example 1. Production of LNP 1 (mRNA: Ovalbumin (OVA) mRNA)

An OVA mRNA aqueous solution (mRNA concentration: 70 μg/mL, solvent: 25 mM NaAc, 154 mM NaCl, pH=4.5)

was prepared (solution A). A lipid ethanol solution (lipid concentration: 8 mM) in which ALC-0315([(4-hydroxybutyl)azanediyl]di(hexane-6,1-diyl)bis(2-hexyldecanoate)), DSPC (distearoylphosphatidylcholine), DMG-PEG200 (1,2-dimyristoyl-sn-glycero-3-methoxypolyethylene glycol), and cholesterol were mixed in a ratio (molar ratio) of ALC-0315([(4-hydroxybutyl)azanediyl]di(hexane-6,1-diyl) bis(2-hexyldecanoate)):DSPC (distearoylphosphatidylcholine):DMG-PEG200 (1,2-dimyristoyl-sn-glycero-3-methoxypolyethylene glycol):Cholesterol=50:10:1.5:38.5 was prepared (solution B). Using an iLiNP microchannel chip ((Lilac Pharma) or NanoAssemblr (Precision NanoSystems), solutions A and B individually prepared were mixed at a flow rate of 500 μL/min (iLiNP microchannel chip) or at a flow rate of 12 mL/min (NanoAssemblr) (flow rate ratio: A:B=3). The mixed solution underwent solvent substitution with PBS using a dialysis membrane (MWCO; 3.5 K). The collected solution was concentrated 5-fold using an Amicon tube (MWCO; 30K) and passed through a 0.45-μm filter to obtain an LNP (OVA) solution (mass average particle size: 81 nm, ELSZ-2000ZS produced by Otsuka Electronics Co., Ltd.) A Ribo Green Assay (Invitrogen) was performed, thus calculating 185 μg/mL as the mRNA concentration.

Reference Example 2. Production of LNP 2 (mRNA: EGFP mRNA)

An LNP (EGFP) solution was obtained in the same manner as in Reference Example 1, except that the mRNA of EGFP, which is a fluorescent protein, was used in place of the OVA mRNA (mass average particle size: 75 nm, mRNA concentration: 186 μg/mL).

Reference Example 3. Production of LNP 3 (mRNA: HPV E7 mRNA)

An LNP (HPV E7) solution is obtained in the same manner as in Reference Example 1, except that the mRNA of E7 protein of a human papillomavirus is used in place of the OVA mRNA.

Example 1. Production of CHP:LNP 1 (mRNA: OVA mRNA)

The same amount of 10 mg/mL CHP aqueous solution was added to 1 mL of the LNP (OVA) solution (Reference Example 1), followed by stirring for 30 minutes. The mixture was passed through a 0.45-μm filter to obtain a CHP:LNP (OVA) solution (mass average particle size: 122 nm, mRNA concentration: 93 μg/mL) (Method 1).

Example 2. Production of CHP:LNP 2 (mRNA: EGFP mRNA)

A CHP:LNP (EGFP) solution was obtained in the same manner as in Example 1, except that the LNP (EGFP) solution (Reference Example 2) was used in place of the LNP (OVA) solution (Reference Example 1) (mass average particle size: 117 nm, mRNA concentration: 95 μg/mL) (Method 1).

Example 3. Production of CHP:LNP 3 (mRNA: HPV E7 mRNA)

A CHP:LNP (HPV E7) solution is obtained in the same manner as in Example 1, except that the LNP (HPV E7) solution (Reference Example 3) is used in place of the LNP (OVA) solution (Reference Example 1) (Method 1).

Example 4. Production of CHP:LNP 1 (mRNA: OVA mRNA)

An OVA mRNA aqueous solution (mRNA concentration: 70 μg/mL, solvent: 1 mg/mL CHP in 25 mM NaAc, 154 mM NaCl, pH=4.0) was prepared (solution A). A lipid ethanol solution (lipid concentration: 8 mM) in which MC3, DSPC, and cholesterol were mixed in a ratio (molar ratio) of MC3:DSPC:Cholesterol=50:10:40 was prepared (solution B). Using an iLiNP microchannel chip or NanoAssemblr, solutions A and B prepared individually were mixed at a flow rate of 500 μL/min (iLiNP microchannel chip) or at a flow rate of 12 mL/min (NanoAssemblr) (flow rate ratio: A:B=3). The mixed solution underwent solvent substitution with PBS using a dialysis membrane (MWCO; 3.5 K). The collected solution was concentrated 5-fold using an Amicon tube (MWCO; 30K) and passed through a 0.45-μm filter to obtain a CHP:LNP (OVA) solution (mass average particle size: 155 nm, mRNA concentration: 70 μg/mL) (Method 2).

Example 5. Production of CHP:LNP 5 (mRNA: EGFP mRNA)

An EGFP mRNA aqueous solution (mRNA concentration: 70 μg/mL, solvent: 2 mg/mL CHP in 25 mM NaAc, 154 mM NaCl, pH=4.0) was prepared (solution A). A lipid ethanol solution (lipid concentration: 8 mM) in which ALC-0315, DSPC, and cholesterol were mixed in the ratio (molar ratio) of ALC-0315:DSPC:Cholesterol=45.5:9:45.5 was prepared (solution B). Using an iLiNP microchannel chip or NanoAssemblr, solutions A and B individually prepared were mixed at a flow rate of 500 μL/min (iLiNP microchannel chip) or at a flow rate of 12 mL/min (NanoAssemblr) (flow rate ratio: A:B=3). The mixed solution underwent solvent substitution with PBS using a dialysis membrane (MWCO; 3.5 K). The collected solution was concentrated 5-fold using an Amicon tube (MWCO; 30K) and passed through a 0.45-μm filter to obtain an CHP:LNP (EGFP) solution (weight average particle size: 135 nm, mRNA concentration: 82 μg/mL (Method 2).

Example 6. Production of CHP:LNP 6 (mRNA: HPV E7 mRNA)

A CHP:LNP (HPV E7) solution is obtained in the same manner as in Example 4 except that HPV E7 mRNA is used in place of the OVA mRNA (Method 2).

Examples 7 to 23. Production of CHP:LNP 7

Using methods (Methods 1 and 2) shown below, nucleic acids, ionized lipids, and lipid ratios shown in the table below, CHP:LNP were produced. The production compositions and physical properties of the CHP:LNP produced in Examples 1 to 23 are shown in the following table.

TABLE 1

| Example | Method | Nucleic acid | Ionized lipid IL | Lipid ratio IL:PL:PEG:Chol | Particle size nm | mRNA concentration mg/mL | Inclusion rate (%) | CHP concentration mg/mL |
|---|---|---|---|---|---|---|---|---|
| 1 | 1 | OVA | ALC-0315 | 50:10:1.5:38.5 | 122 | 0.09 | 83 | 5 |
| 2 | 1 | EGFP | ALC-0315 | 50:10:1.5:38.5 | 117 | 0.095 | 90 | 5 |
| 3 | 1 | HPV E7 | ALC-0315 | 50:10:1.5:38.5 | | | | |
| 4 | 2 | OVA | ALC-0315 | 50:10:0:40 | 155 | 0.07 | 92 | 2 |
| 5 | 2 | EGFP | ALC-0315 | 45.5:9:0:45.5 | 135 | 0.082 | 94 | 4 |
| 6 | 2 | HPV E7 | ALC-0315 | 50:10:0:40 | | | | |
| 7 | 1 | EGFP | DOTAP | 50:10:0:40 | 188 | 0.069 | 85 | 5 |
| 8 | 1 | EGFP | DOTAP | 50:10:1.5:38.5 | 154 | 0.09 | 95 | 5 |
| 9 | 1 | GFP | DOTAP | 50:10:0:40 | 181 | 0.079 | 90 | 5 |
| 10 | 1 | GFP | DOTAP | 50:10:1.5:38.5 | 134 | 0.084 | 96 | 5 |
| 11 | 1 | GFP | ALC-0315 | 50:10:1.5:38.5 | 126 | 0.1 | 92 | 5 |
| 12 | 1 | EGFP | MC3 | 50:10:1.5:38.5 | 126 | 0.072 | 90 | 5 |
| 13 | 1 | EGFP | SM-102 | 50:10:1.5:38.5 | 142 | 0.077 | 90 | 5 |
| 14 | 1 | EGFP | DODAP | 50:10:1.5:38.5 | 145 | 0.075 | 76 | 5 |
| 15 | 1 | OVA | MC3 | 50:10:1.5:38.5 | 130 | 0.093 | 91 | 5 |
| 16 | 2 | OVA | MC3 | 50:10:0:40 | 105 | 0.1 | 28 | 2 |
| 17 | 2 | EGFP | ALC-0315 | 62.5:13:0:25 | 182 | 0.07 | 74 | 10 |
| 18 | 1 | CpG2395 | DOTAP | 50:19.5:0.5:30 | 193 | 0.095 | 96 | 5 |
| 19 | 1 | EGFP | CL4H6 | 50:10:1.5:38.5 | 188 | 0.06 | 34 | 5 |
| 20 | 2 | EGFP | CL4H6 | 45.5:9:0:45.5 | 142 | 0.035 | 88 | 4 |
| 21 | 2 | CpG2395 | ALC-0315 | 45.5:9:0:45.5 | 124 | 0.048 | 96 | 4 |
| 22 | 1 | EGFP | CL15H6 | 50:10:1.5:38.5 | 166 | 0.059 | 82 | 5 |
| 23 | 2 | EGFP | CL15H6 | 45.5:9:0:45.5 | 148 | 0.057 | 95 | 4 |

Example 58. Production 8 of CHP:LNP (mRNA: mCherry mRNA)

An aqueous mCherry mRNA solution (mRNA concentration: 70 μg/mL, solvent: 25 mM NaAc, 154 mM NaCl, pH=4.0) was prepared (solution A). An ethanol solution of lipids (lipid concentration: 8 mM) mixed at a mixing ratio (molar ratio) of SM-102:DSPC:Cholesterol=45.5:9:45.5 was prepared (solution B). Further, a pullulan nanogel solution (CHP concentration: 2 mg/mL, solvent: PBS) was prepared (solution C) by the method described in Preparation Example 1. The solutions prepared individually were mixed at a flow rate of 12 mL/min (flow ratio rate: A:B:C=1:3:2.46) using NanoAssemblr (produced by Precision NanoSystems Inc.). The mixed solution was filtered through a dialysis membrane (MWCO; 10 K) and the solvent was replaced with PBS. The collected solution was concentrated 7-fold using an Amicon tube (MWCO; 100K) and passed through a 0.45 μm filter to obtain a CHP:LNP (mCherry) solution (weight average particle size: 131 nm, mRNA concentration: 135 μg/mL) (Method 3).

Examples 24 to 57 and 59 to 62. Production 9 of CHP:LNP

Using the production methods (Methods 1, 2, and 3), nucleic acids, ionized lipids, phospholipids, PEG-modified lipids, lipid ratio, and CHP concentrations shown below in Tables 2 and 3, CHP:LNP solutions were produced. The formulations of the CHP:LNP solutions produced in Examples 24 to 62 and their physical properties, as well as those of Examples 1 to 23, are shown in the following tables.

TABLE 2

| Example | Method | Nucleic acid | Ionized lipid IL | Phospholipid PL | PEG lipid PEG | Lipid ratio IL:PL:PEG:Chol | Particle size nm | mRNA concen-tration mg/mL | Inclusion rate % | CHP concen-tration mg/mL |
|---|---|---|---|---|---|---|---|---|---|---|
| 1 | 1 | OVA | ALC-0315 | DSPC | DMG-PEG2000 | 50:10:1.5:38.5 | 122 | 0.09 | 83 | 5.00 |
| 2 | 1 | EGFP | ALC-0315 | DSPC | DMG-PEG2000 | 50:10:1.5:38.5 | 117 | 0.095 | 90 | 5.00 |
| 3 | 1 | HPV E7 | ALC-0315 | DSPC | DMG-PEG2000 | 50:10:1.5:38.5 | | | | |
| 4 | 2 | OVA | ALC-0315 | DSPC | — | 50:10:0:40 | 155 | 0.07 | 92 | 2.00 |
| 5 | 2 | EGFP | ALC-0315 | DSPC | — | 45.5:9:0:45.5 | 135 | 0.082 | 94 | 4.00 |
| 6 | 2 | HPV E7 | ALC-0315 | DSPC | — | 50:10:0:40 | | | | |
| 7 | 1 | EGFP | DOTAP | DSPC | — | 50:10:0:40 | 188 | 0.069 | 85 | 5.00 |
| 8 | 1 | EGFP | DOTAP | DSPC | DMG-PEG2000 | 50:10:1.5:38.5 | 154 | 0.09 | 95 | 5.00 |
| 9 | 1 | GFP | DOTAP | DSPC | — | 50:10:0:40 | 181 | 0.079 | 90 | 5.00 |
| 10 | 1 | GFP | DOTAP | DSPC | DMG-PEG2000 | 50:10:1.5:38.5 | 134 | 0.084 | 96 | 5.00 |
| 11 | 1 | GFP | ALC-0315 | DSPC | DMG-PEG2000 | 50:10:1.5:38.5 | 126 | 0.1 | 92 | 5.00 |
| 12 | 1 | EGFP | MC3 | DSPC | DMG-PEG2000 | 50:10:1.5:38.5 | 126 | 0.072 | 90 | 5.00 |
| 13 | 1 | EGFP | SM-102 | DSPC | DMG-PEG2000 | 50:10:1.5:38.5 | 142 | 0.077 | 90 | 5.00 |
| 14 | 1 | EGFP | DODAP | DSPC | DMG-PEG2000 | 50:10:1.5:38.5 | 145 | 0.075 | 76 | 5.00 |
| 15 | 1 | OVA | MC3 | DSPC | DMG-PEG2000 | 50:10:1.5:38.5 | 130 | 0.093 | 91 | 5.00 |
| 16 | 2 | OVA | MC3 | DSPC | — | 50:10:0:40 | 105 | 0.1 | 28 | 2.00 |
| 17 | 2 | EGFP | ALC-0315 | DSPC | DMG-PEG2000 | 2.562.5:13:0:25 | 182 | 0.07 | 74 | 10.00 |
| 18 | 1 | CpG2395 | DOTAP | DSPC | DMG-PEG2000 | 50:19.5:0.5:30 | 193 | 0.095 | 96 | 5.00 |
| 19 | 1 | EGFP | CL 4H6 | DSPC | DMG-PEG2000 | 50:10:1.5:38.5 | 188 | 0.06 | 34 | 5.00 |
| 20 | 2 | EGFP | CL 4H6 | DSPC | — | 45.5:9:0:45.5 | 143 | 0.035 | 88 | 4.00 |
| 21 | 2 | CpG2395 | ALC-0315 | DSPC | — | 45.5:9:0:45.5 | 124 | 0.048 | 96 | 4.00 |
| 22 | 1 | EGFP | CL 15H6 | DSPC | DMG-PEG2000 | 50:10:1.5:38.5 | 166 | 0.059 | 82 | 5.00 |

TABLE 2-continued

| Example | Method | Nucleic acid | Ionized lipid IL | Phospholipid PL | PEG lipid PEG | Lipid ratio IL:PL:PEG:Chol | Particle size nm | mRNA concen-tration mg/mL | Inclusion rate % | CHP concen-tration mg/mL |
|---|---|---|---|---|---|---|---|---|---|---|
| 23 | 2 | EGFP | CL 15H6 | DSPC | — | 45.5:9:0:45.5 | 148 | 0.057 | 95 | 4.00 |
| 24 | 1 | mCherry | ALC-0315 | DSPC | DMG-PEG2000 | 50:10:1.5:38.5 | 123 | 0.069 | 89 | 5.00 |
| 25 | 2 | mCherry | ALC-0315 | DSPC | — | 45.5:9:0:45.5 | 128 | 0.078 | 92 | 4.00 |
| 26 | 1 | EGFP | ALC-0315 | DSPC | DMG-PEG2000 | 50:10:1.5:38.5 | 82 | 0.144 | 95 | 0.03 |
| 27 | 1 | EGFP | ALC-0315 | DSPC | DMG-PEG2000 | 50:10:1.5:38.5 | 85 | 0.141 | 96 | 0.06 |
| 28 | 1 | EGFP | ALC-0315 | DSPC | DMG-PEG2000 | 50:10:1.5:38.5 | 85 | 0.138 | 97 | 0.12 |
| 29 | 1 | EGFP | ALC-0315 | DSPC | DMG-PEG2000 | 50:10:1.5:38.5 | 90 | 0.114 | 98 | 0.21 |
| 30 | 2 | EGFP | ALC-0315 | DSPC | — | 45.5:9:0:45.5 | 207 | 0.068 | 92 | 0.15 |
| 31 | 2 | EGFP | ALC-0315 | DSPC | — | 45.5:9:0:45.5 | 147 | 0.115 | 93 | 1.50 |

TABLE 3

| Example | Method | Nucleic acid | Ionized lipid IL | Phospholipid PL | PEG lipid PEG | Lipid ratio IL:PL:PEG:Chol | Particle size nm | mRNA concen-tration mg/mL | Inclusion rate % | CHP concen-tration mg/mL |
|---|---|---|---|---|---|---|---|---|---|---|
| 32 | 1 | mCherry | ALC-0315 | DSPC | DMG-PEG2000 | 50:10:1.5:38.5 | 94 | 0.080 | 96 | 0.03 |
| 33 | 1 | mCherry | ALC-0315 | DSPC | DMG-PEG2000 | 50:10:1.5:38.5 | 97 | 0.076 | 97 | 0.06 |
| 34 | 1 | mCherry | ALC-0315 | DSPC | DMG-PEG2000 | 50:10:1.5:38.5 | 103 | 0.057 | 97 | 0.12 |
| 35 | 1 | mCherry | ALC-0315 | DSPC | DMG-PEG2000 | 50:10:1.5:38.5 | 102 | 0.053 | 97 | 0.21 |
| 36 | 1 | EGFP | ALC-0315 | DSPC | DMG-PEG2000 | 50:10:1.5:38.5 | 109 | 0.096 | 99 | 0.62 |
| 37 | 1 | EGFP | ALC-0315 | DSPC | DMG-PEG2000 | 50:10:1.5:38.5 | 111 | 0.097 | 99 | 1.14 |
| 38 | 1 | EGFP | ALC-0315 | DSPC | DMG-PEG2000 | 50:10:1.5:38.5 | 116 | 0.087 | 98 | 1.90 |
| 39 | 1 | mCherry | ALC-0315 | DSPC | ALC-0159 | 46.3:9.4:1.6:42.7 | 101 | 0.130 | 99 | 0.62 |
| 40 | 1 | mCherry | ALC-0315 | DSPC | ALC-0159 | 46.3:9.4:1.6:42.7 | 105 | 0.125 | 99 | 1.14 |
| 41 | 1 | mCherry | ALC-0315 | DSPC | ALC-0159 | 46.3:9.4:1.6:42.7 | 111 | 0.113 | 98 | 1.90 |
| 42 | 1 | mCherry | CL 15H6 | DSPC | ALC-0159 | 46.3:9.4:1.6:42.7 | 152 | 0.122 | 92 | 0.62 |
| 43 | 1 | mCherry | CL 15H6 | DSPC | ALC-0159 | 46.3:9.4:1.6:42.7 | 155 | 0.117 | 92 | 1.14 |
| 44 | 1 | Cy5-Luc | ALC-0315 | DSPC | ALC-0159 | 46.3:9.4:1.6:42.7 | 106 | 0.061 | 97 | 1.50 |
| 45 | 1 | mCherry | CL 1H6 | DSPC | ALC-0159 | 46.3:9.4:1.6:42.7 | 143 | 0.101 | 99 | 1.50 |
| 46 | 1 | Cyclic EGFP | ALC-0315 | DSPC | ALC-0159 | 46.3:9.4:1.6:42.7 | 107 | 0.169 | 98 | 1.41 |
| 47 | 1 | Luc | ALC-0315 | DSPC | ALC-0159 | 46.3:9.4:1.6:42.7 | 113 | 0.203 | 96 | 1.45 |
| 48 | 1 | mCherry | MC3 | DSPC | DMG-PEG2000 | 50:10:1.5:38.5 | 129 | 0.203 | 98 | 1.50 |
| 49 | 1 | mCherry | SM-102 | DSPC | DMG-PEG2000 | 50:10:1.5:38.5 | 124 | 0.204 | 97 | 1.41 |
| 50 | 1 | mCherry | SM-102 | DSPC | DMG-PEG2000 | 50:10:1.5:38.5 | 116 | 0.140 | 99 | 1.46 |
| 51 | 1 | mCherry | SM-102 | DSPC | DMG-PEG2000 | 50:10:1.5:38.5 | 122 | 0.136 | 98 | 2.52 |
| 52 | 1 | mCherry | SM-102 | DSPC | DMG-PEG2000 | 50:10:1.5:38.5 | 124 | 0.092 | 95 | 4.04 |
| 53 | 2 | mCherry | SM-102 | DSPC | — | 45.5:9:0:45.5 | 170 | 0.241 | 97 | 0.75 |
| 54 | 1 | mCherry | SM-102 | DSPC | DSG-PEG2000 | 50:10:1.5:38.5 | 123 | 0.229 | 98 | 1.41 |
| 55 | 1 | mCherry | SM-102 | DSPC | DSG-PEG2000 | 50:6.5:5:38.5 | 92 | 0.175 | 94 | 1.41 |
| 56 | 1 | mCherry | SM-102 | DOPE | DSG-PEG2000 | 50:25:2.5:22.5 | 105 | 0.219 | 96 | 1.41 |
| 57 | 2 | mCherry | ALC-0315 | DSPC | — | 45.5:9:0:45.5 | 217 | 0.152 | 95 | 1.5 |
| 58 | 3 | mCherry | SM-102 | DSPC | — | 45.5:9:0:45.5 | 131 | 0.135 | 98 | 0.761 |
| 59 | 3 | mCherry | SM-102 | DSPC | — | 45.5:9:0:45.5 | 144 | 0.107 | 99 | 0.38 |
| 60 | 1 | mCherry | SM-102 | DSPC | DMG-PEG2000 | 50:25:2.5:22.5 | 102 | 0.223 | 94 | 1.4 |
| 61 | 3 | mCherry | CL 15H6 | DSPC | — | 45.5:9:0:45.5 | 114 | 0.089 | 95 | 0.911 |
| 62 | 3 | mCherry | SM-102 | DSPC | — | 45.5:9:0:45.5 | 111 | 0.149 | 83 | 1.521 |

In particular, when no or small amounts of PEG-modified lipids were added, the desired LNP often could not be produced by precipitation or very large particles with a particle size of 200 nm or more were formed. It was thus impossible to create an LNP 5 that contributes to administration into the body. Unexpectedly, however, when CHP was added, LNPs with an ideal particle size could be produced in all of the Examples 1 to 62 of the present invention.

Test Example 1. Test of Evaluating Antigenicity by Immunization of Mice

CHP:LNP (OVA) (Examples 1 and 4) or LNP (OVA) (Reference Example 1) (the mRNA level being 10 μg per each) is subcutaneously administered to C57BL/6 mice (Japan SLC). As a comparison, the same dose of CHP:LNP (OVA) or LNP (OVA) is intramuscularly administered to other mice. Three weeks later, administration is conducted at the same dose and by the same administration method; and one another week later, a blood sample, a splenocyte, and a regional lymph node are taken.

The splenocyte is promptly collected and stimulated with the CD4 epitope peptide of OVA (ROCOLAND, Ovalbumin 323-339-OH) and the CD8 epitope peptide of OVA (ROCOLAND, OVA 257-264). Secreted IFN-γ is measured by ELISA, and intracellular IFN-γ, IL-2, and TNFα are measured using an intracellular cytokine staining method.

For the regional lymph node-derived cell and collected splenocyte, expression analysis is performed with multiple cell surface markers (CD3, CD4, CD8, CD127, CD62L, CD44, KLRG1, Tim-3, Lag-3, and PD-1) to analyze T-cell status.

Using an antibody (BioLegend) recognizing an OVA antigen and a MHC complex, the frequency of an antigen-presenting cell and the presented OVA antigen amount are measured. In the measurement, co-staining of CD11b, CD11c, F4/80, B220, CD8a, etc., as cell surface markers is performed to identify the antigen-presenting cell. Using an antibody against SIGN-R[1], whether uptake of the antigen-presenting cell is receptor-dependent is evaluated.

The OVA-specific antibody in serum is measured by ELISA.

Test Example 2. Test of Comparing Toxicity of CHP:LNP (OVA) and LNP (OVA)

(1) Cytokine Release Syndrome

CHP:LNP (OVA) (Examples 1 and 4) or LNP (OVA) (Reference Example 1) (the mRNA level being 10 μg per each) is subcutaneously administered to C57BL/6 mice. Blood samples are taken over time, and the blood concentration of IL-6, IL-1l, etc. is measured by ELISA or using a multiplex bead-based assay panel (BioLegend).

(2) Skin Irritation at the Site of Administration

CHP:LNP (OVA) (Examples 1 and 4) or LNP (OVA) (Reference Example 1) (the mRNA level being 10 μg per each) is subcutaneously administered to C57BL/6 mice. 24 hours later, skin at the administration site is extracted. After observing skin flushing, the number of infiltrating lymphocytes is measured.

(3) Weight Fluctuation

CHP:LNP (OVA) (Examples 1 and 4) or LNP (OVA) (Reference Example 1) (the mRNA level being 10 μg per each) is subcutaneously administered to C57BL/6 mice. Thereafter, the weight change is measured over time.

(4) Body Temperature Fluctuation

CHP:LNP (OVA) (Examples 1 and 4) or LNP (OVA) (Reference Example 1) (the mRNA level being 10 μg per each) is subcutaneously administered to C57BL/6 mice. Thereafter, the rectal temperature is measured over time.

Test Example 3. Test of Evaluating Vaccine by Immunization of Mice

Immunization is performed on C57BL/6 mice by subcutaneous administration of CHP:LNP (HPV E7) (Example 6) or LNP (HPV E7) (Reference Example 3) (the mRNA level being 10 μg per each). Two or three weeks later, the second immunization is performed at the same dose. On the same day, $1\times10^5$ HPV E7 protein-stable expressing mouse lung cancer cell lines (TC-1 cells) are subcutaneously transplanted. Thereafter, the tumor size is measured over time.

Test Example 4. Immunogenicity Test

CHP:LNP (OVA) (Examples 1 and 4) or LNP (OVA) (Reference Example 1) (the mRNA level being 10 μg per each) is subcutaneously administered to C57BL/6 mice. Thereafter, subcutaneous administration is performed multiple times (2 to 5 times) at the same dose at 2- or 3-week intervals. The anti-PEG antibody level and the anti-CHP antibody level in the blood are then measured by ELISA.

Test Example 5. Test of Evaluating Function in Human Peripheral Blood Lymphocyte-derived Macrophage CD14-positive monocytes were isolated from human peripheral blood, and seeded in 500 μL of basic medium (RPMI, 10% fetal bovine serum, 50 ng/mL M-CSF) in a 24-well tissue culture plate at $2\times10^5$ cells/well, followed by 5% $CO_2$ incubator at 37° C. for 3 days. Thereafter, medium replacement with 500 μL of basic medium was conducted, followed by culture for another 3 days.

Induction of differentiation of M0 macrophages was performed by replacement with 500 μL of basic medium, while induction of differentiation of M2-like macrophages was performed by replacement with 500 μL of medium for differentiation induction, which was obtained by adding 50 ng/mL of IL-4, 50 ng/mL of IL-6, and 50 ng/mL of IL-10, and 50 ng/mL of IL-13 to the basic medium, followed by culture for two days. CHP:LNP (EGFP) (Examples 2 and 5) or LNP (EGFP) (Reference Example 2) (the mRNA level being 0.5 μg per each) was added to the basic medium, and culture was performed under 4° C. conditions for 2 hours. Thereafter, replacement with 500 μL of medium was performed, followed by incubation at 37° C., 5% $CO_2$, overnight. Thereafter, the cells were washed with PBS, and then 200 μL of a cell dissociation solution (Biological Industries) was added, followed by incubation at 37° C. for 20 min. 200 μL of a wash solution (Miltenyi) was added, and cells were peeled off by pipetting, followed by centrifugation at 500 g for 5 minutes, thus collecting cells. Thereafter, staining with a PB450-labeled anti-CD206 antibody (BD Biosciences) and an APC-labeled anti-DC-SIGN antibody (R&D Systems) was performed, followed by analysis with flow cytometry.

Test Results

Figure 2:
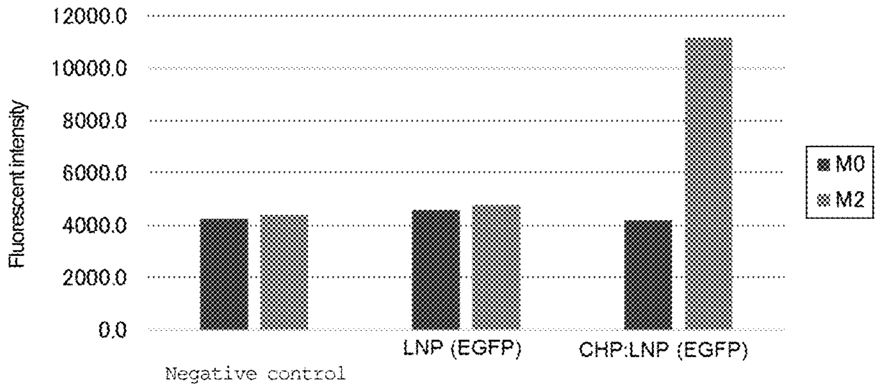
FIG. 2 shows the results of Test Example 5 in which after the addition of LNP, treatment was performed at 4° C. for 2 hours, followed by replacement of medium and further incubation at 37° C. overnight. The items in the figure have the same meanings as in FIG. 1.
Figure 3:
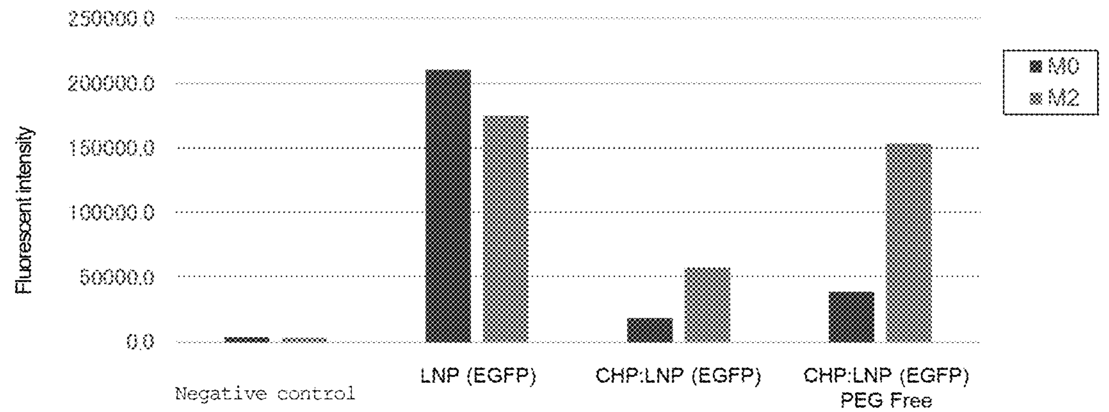
FIG. 3 shows the results of Test Example 5 in which after the addition of LNP, incubation was performed at 37° C. overnight without treatment at 4° C. The items in the figure have the same meanings as in FIG. 1.

FIG. 1 shows the results of the case in which after the addition of CHP:LNP (EGFP) (Example 2) or LNP (EGFP), incubation was performed at 37° C. overnight without treatment at 4° C. FIG. 2 shows the results of the case in which after the addition of CHP:LNP (EGFP) (Example 2) or LNP (EGFP), treatment at 4° C. for 2 hours was performed, the medium was then replaced, and incubation was performed at 37° C. overnight. FIG. 3 shows the results of other experiments in which after the addition of CHP:LNP (EGFP) (Example 2), PEG-free CHP:LNP (EGFP) (Example 5) or LNP (EGFP), incubation at 37° C. overnight was performed.

Test Example 6. Experiment for Confirming Expression in Antigen-Presenting Cell by Subcutaneous Administration in Mice CHP:LNP (EGFP) (Example 5) or LNP (EGFP) (Reference Example 2) (the mRNA level being 10 μg per each) is subcutaneously administered to C57BL/6 mice. After 24 hours, the inguinal lymph nodes are extracted, and cells are collected and analyzed by flow cytometry.

Test Example 7. Measurement of Particle Size Before and After Freezing and Melting CHP:LNP solutions (Examples 19, 20, 23, 26-54, and 57-62) were frozen at −30° C. once and then thawed. Before and after the freezing and melting, the particle size was measured. For comparison, LNP solutions having the same formulations as the CHP:LNP solutions except for not containing CHP (Reference Examples 19, 26, 32, 36, 39, 42, 44-50, 54, and 60) were also frozen at −30° C. once and then thawed, and the particle size before and after the freezing and melting was measured.

Test Results

Table 4 below shows the results obtained. The comparative LNP solutions not containing CHP were increased in particle size by only one cycle of freezing and melting, whereas the CHP:LNP solutions were unexpectedly suppressed from increasing in particle size before and after freezing and melting. The above results indicate that the CHP has an effect of improving the stability of LNP.

TABLE 4

| CHP:LNP | | | | LNP | | | |
|---|---|---|---|---|---|---|---|
| | Particle size (nm) | | | | Particle size (nm) | | |
| Example | Before freezing and melting | After freezing and melting | Increase rate (%) | Reference example | Before freezing and melting | After freezing and melting | Increase rate (%) |
| 19 | 188 | 226 | 120 | 19 | 142 | 414 | 291 |
| 20 | 143 | 142 | 99 | | — | | |
| 23 | 148 | 149 | 100 | | | | |
| 26 | 82 | 103 | 125 | 26 | 78 | 121 | 155 |
| 27 | 85 | 92 | 108 | | | | |
| 28 | 85 | 90 | 106 | | | | |
| 29 | 90 | 91 | 101 | | | | |
| 30 | 207 | 205 | 99 | | — | | |
| 31 | 147 | 147 | 100 | | | | |
| 32 | 94 | 94 | 99 | 32 | 79 | 114 | 145 |
| 33 | 97 | 96 | 99 | | | | |
| 34 | 103 | 103 | 100 | | | | |
| 35 | 102 | 102 | 100 | | | | |
| 36 | 109 | 108 | 99 | 36 | 83 | 105 | 126 |
| 37 | 111 | 113 | 101 | | | | |
| 38 | 116 | 114 | 99 | | | | |
| 39 | 101 | 103 | 102 | 39 | 73 | 93 | 127 |
| 40 | 105 | 111 | 105 | | | | |
| 41 | 111 | 112 | 101 | | | | |
| 42 | 152 | 162 | 106 | 42 | 129 | 177 | 136 |
| 43 | 155 | 161 | 104 | | | | |
| 44 | 106 | 108 | 102 | 44 | 75 | 100 | 133 |
| 45 | 146 | 159 | 108 | 45 | 114 | 139 | 122 |
| 46 | 107 | 109 | 102 | 46 | 77 | 108 | 141 |
| 47 | 113 | 114 | 101 | 47 | 82 | 142 | 173 |
| 48 | 129 | 132 | 102 | 48 | 97 | 155 | 159 |
| 49 | 121 | 128 | 106 | 49 | 92 | 133 | 145 |
| 50 | 116 | 118 | 102 | 50 | 85 | 120 | 141 |
| 51 | 122 | 122 | 100 | | | | |
| 52 | 124 | 127 | 102 | | | | |
| 53 | 170 | 162 | 95 | | — | | |
| 54 | 123 | 125 | 102 | 54 | 91 | 163 | 179 |
| 57 | 217 | 203 | 94 | | | | |
| 58 | 131 | 129 | 98 | | | | |
| 59 | 144 | 144 | 100 | | | | |
| 60 | 102 | 106 | 104 | 60 | 80 | 95 | 119 |
| 61 | 114 | 119 | 104 | | — | | |
| 62 | 111 | 113 | 102 | | | | |

Test Example 8. Test of Evaluating Function in Human Peripheral Blood Lymphocyte-Derived Macrophage M0 macrophages and M2-like macrophages were prepared in the same manner as in Test Example 5. CHP:LNP (mCherry) solutions (Examples 51, 58, and 61) containing CHP and LNP in an amount of 0.5 μg each in terms of RNA levels or an LNP (mCherry) solution (Reference Example 50) were added to basal media and the cells were incubated overnight at 37° C. and 5% $CO_2$ overnight. Then, after washing with PBS, 200 μL of a Cell Dissociation solution (produced by Biological Industries) was added and the cells were incubated at 37° C. for 20 minutes. Further, 200 μL of a Wash solution (produced by Miltenyi Biotec) was added and the cells were detached by pipetting and subjected to centrifugation at 500 g for 5 minutes to collect the cells. The cells were then stained with PB450-labeled anti-CD206 antibody (produced by BD Biosciences) and APC-labeled anti-DC-SIGN antibody (produced by R&D Systems) and analyzed with a flow cytometer.

Test Results

Figure 4:
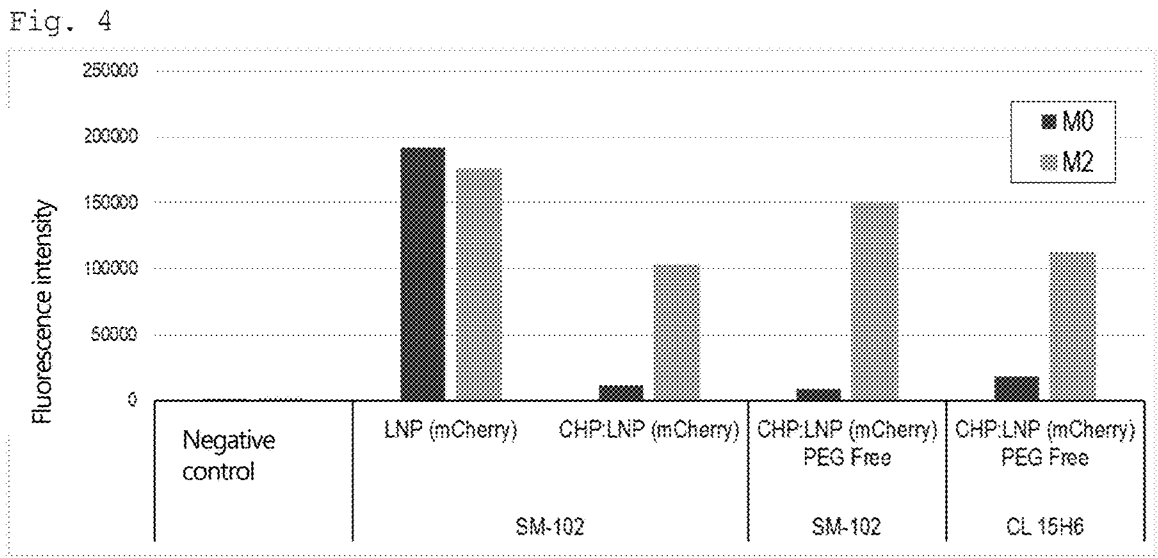
FIG. 4 shows the results of Test Example 8 in which after the addition of LNP, incubation was performed at 37° C. overnight without treatment at 4° C. The items in the figure have the same meanings as in FIG. 1.

FIG. 4 shows the results. Only when CHP-conjugated LNP (CHP:LNP) was used, the expression of the protein in M2-like macrophages, which are DC-SIGN-positive cells, was higher than that in M0 macrophages, which are DC-SIGN-negative cells. From the above, it was found that CHP-conjugated LNP can selectively deliver mRNA to DC-SIGN-positive cells without using ionized lipids and has the ability to express a protein from loaded mRNA.

Test Example 9. Immunogenicity Test-2

CHP:LNP (mCherry) (Example 40), CHP:LNP (mCherry) without PEG-modified lipids (Example 57), or LNP (mCherry) (Reference Example 39) was subcutaneously administered to C57BL/6 mice in an amount of 10 μg per mouse in terms of mRNL levels. Each test group was set to n=5. After another 3 weeks, subcutaneous administration was performed again at the same dose. After 1 week, the amount of anti-PEG antibody in the blood was measured by the ELISA method (Life Diagnostics). As a negative control, the solvent alone (PBS) was administered.

Test Results

Figure 5:
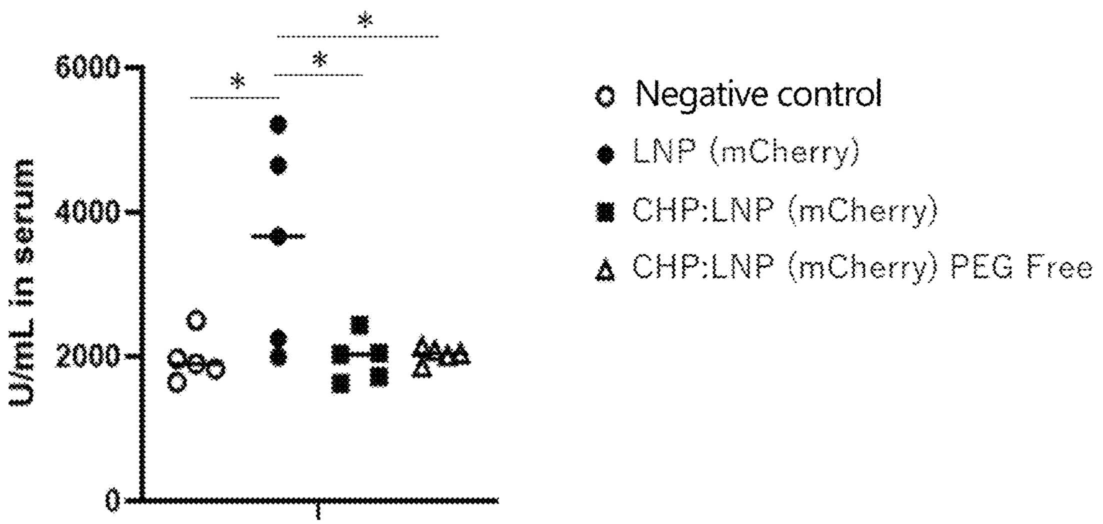
FIG. 5 shows the results of Test Example 9 in which after LNP administration, PEG antibody in blood was measured. The negative control shows the results obtained without administering LNP.

FIG. 5 shows the obtained results. As compared to the negative control, the CHP-conjugated LNP (CHP:LNP (mCherry)) administration group, and the PEG-modified lipid-free, CHP-conjugated LNP (PEG-free CHP:LNP (mCherry)) administration group, anti-PEG antibody (IgM) was significantly detected in the LNP (mCherry) administration group (*; $p<0.05$, unpaired t-test). The above results suggest that even when PEG-modified lipids are present, CHP-conjugated LNP has the possibility of avoiding adverse reactions caused by anti-PEG antibody, such as anaphylaxis and the accelerated blood clearance (ABC) phenomenon, in which repeated administration reduces the efficacy of the drug.

Test Example 10. Experiment 1 for Confirming the Expression in Nearby Lymph Nodes by Subcutaneous Administration into Mice CHP:LNP (mCherry) (Example 40) or LNP (mCherry) (Reference Example 39) was injected intradermally around the right dorsal and lumbar region of C57BL/6 mice in an amount of 5 μg per mouse in terms of mRNL levels. Seventeen hours after the administration, the fluorescence intensity of the mCherry protein was detected using an in vivo imaging instrument (produced by Vilber Bio Imaging) to measure the expression of the mCherry protein at the site of administration and in nearby lymph nodes (inguinal lymph nodes). The fluorescent protein was also detected from the removed nearby lymph nodes (transinguinal lymph nodes) at the same wavelength by using the same device.

removed nearby lymph nodes, the expression with CHP: LNP (mCherry) was confirmed to be higher than that with LNP (mCherry). These results show that when administered intradermally, CHP-conjugated LNP has higher capability of delivery to nearby lymph nodes, as compared to LNP.

Test Example 11. Evaluation of Skin Inflammation at the Site of Administration-2

After shaving C57BL/6 mice, CHP:LNP (EGFP) (Example 2) or LNP (EGFP) (Reference Example 2) was administered in an amount of 9.8 μg per mouse in terms of mRNA levels intradermally around the dorsal and lumbar region. Three days after the administration and five days after the administration, skin tissue was collected and fixed in 4% paraformaldehyde for 48 hours. The paraformaldehyde as a fixing solution was then replaced with a 70% ethanol solution. HE staining and immunostaining with anti-IBA1 antibody were then performed and the skin tissue was subjected to pathological observation.

Test Results

Table 5 shows the results. In the LNP (EGFP) administration group, infiltration of inflammatory cells, i.e., an increase in IBA1-positive cells, which is an indicator of activated macrophages, was higher than that of the CHP: LNP (EGFP) administration group. The above results show that the inflammation induced by local administration of lipid nanoparticles can be suppressed by using CHP-conjugated LNP (CHP:LNP) better than by using LNP.

TABLE 5

| | Day 3 | | | | | | Day 5 | | | | | |
|---|---|---|---|---|---|---|---|---|---|---|---|---|
| | Test drug | | | | | | | | | | | |
| | Vehicle | | LNP | | CHP:LNP | | Vehicle | | LNP | | CHP:LNP | |
| | Sample No. | | | | | | | | | | | |
| | 1 | 2 | 5 | 6 | 9 | 10 | 3 | 4 | 7 | 8 | 11 | 12 |
| HE staining | | | | | | | | | | | | |
| Thickening of epidermis | − | − | − | − | ± | − | − | − | + | ± | − | − |
| Inflammatory cellular infiltration of dermis | − | − | + | + | ± | + | − | − | + | + | ± | ± |
| Inflammatory cellular infiltration of the subcutaneous tissue fat layer | − | − | + | + | ± | ± | − | − | + | + | ± | ± |
| Inflammatory cellular infiltration of subfascial tissue | − | − | + | + | ± | + | − | − | ± | + | + | ± |
| Iba1 staining | | | | | | | | | | | | |
| Increased Iba1-positive macrophages in the dermis | − | − | + | + | + | + | − | − | ++ | + | + | + |
| Increased Iba1-positive macrophages in the subcutaneous tissue fat layer | − | − | + | + | + | ± | − | − | + | ++ | + | + |
| Increased Iba1-positive macrophages in subfascial tissue | − | − | + | + | ± | + | − | − | + | ++ | + | + |

−: No abnormal findings
±: Light
+: Light
++: Moderate
+++: Severe

Test Results

Figure 6:
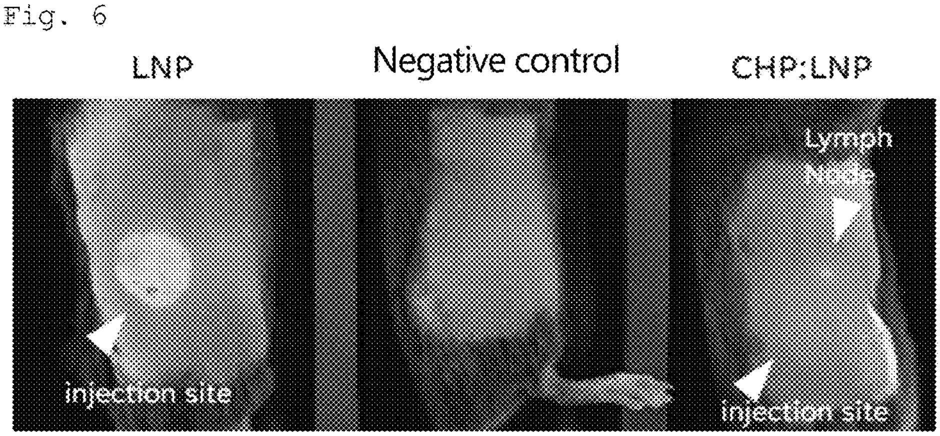
FIG. 6 shows representative results obtained at the site of administration in Test Example 10. The negative control shows results obtained without administering LNP.
Figure 7:
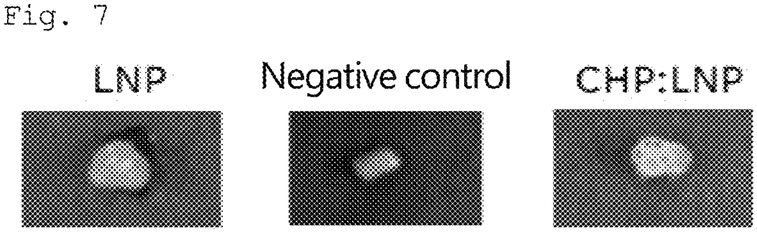
FIG. 7 shows representative results obtained at nearby lymph nodes (inguinal lymph nodes) removed in Test Example 10. Negative controls show the results obtained without administering LNP.

FIG. 6 shows representative results obtained at the site of administration. FIG. 7 shows representative results obtained at removed nearby lymph nodes (inguinal lymph nodes). At the site of administration, a wide expression with LNP (mCherry) was confirmed, but the expression with CHP: LNPs (mCherry) was low. On the other hand, in the nearby lymph nodes, the expression with CHP:LNP (mCherry) was higher than that with LNP (mCherry). Further, in the

Test Example 12. Evaluation of Effects on Body Weight

CHP:LNP(OVA) (Example 1) or LNP(OVA) (Reference Example 1) was subcutaneously administered to C57BL/6 mice in an amount of 10 μg per mouse in terms of mRNA levels (day 0). Further, 3 weeks after the first time administration (day 21), subcutaneous administration was performed again at the same dose. Body weight was continuously measured on each administration day and 2 consecutive days immediately after each administration. The body weight was further measured once a week from the first administration to day 28. Each test group was set to n=3. No drug solution was administered to the comparative group.

Test Results

Figure 8:
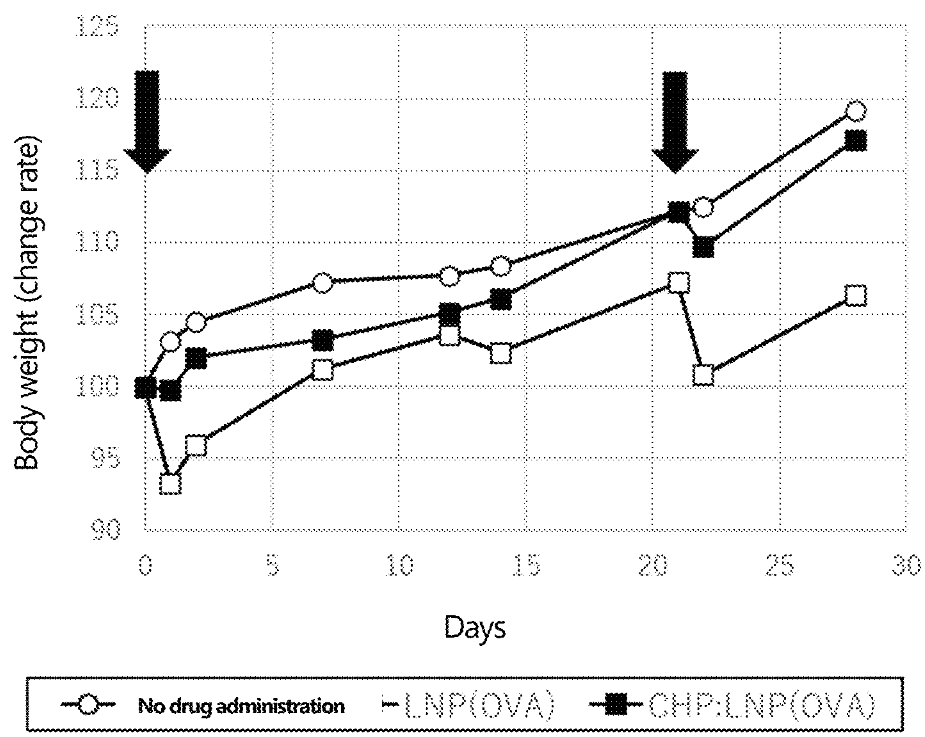
FIG. 8 shows the results of body weight changes over time after administration of LNP in Test Example 12. For comparison, the results obtained without administering LNP are shown.

FIG. 8 shows the results obtained. With the body weight of each group on the first day of administration (day 0) being defined as 100%, graphs were created by using the average values of each group. The arrows in the figure indicate the days on which LNP was administered. The results show that body weight loss on the day after each dose was observed in the LNP administration group, whereas only minor body changes were observed in the CHP-conjugated administration group and the body weight changes were similar to those of the group to which no pharmaceutical drug was administered. The above results show that CHP-conjugated LNP can reduce the side effect of body weight loss caused by LNP.

The invention claimed is:

1. A lipid nano particle comprising an ionized lipid, a phospholipid, and a sterol as lipid components of the lipid nano particle, and a modified polysaccharide containing a hydrophobic group, wherein the content of the ionized lipid is 35 to 70 mol % based on 100 mol % of the lipid components of the lipid nano particle, the content of the phospholipid is 4 to 25 mol % based on 100 mol % of the lipid components of the lipid nano particle, the content of the sterol is 15 to 55 mol % based on 100 mol % of the lipid components of the lipid nano particle, the hydrophobic group includes at least one member selected from a group consisting of a hydrophobic group having a sterol skeleton and a $C_{8-50}$ chain hydrocarbon group, and a polysaccharide that forms the modified polysaccharide comprises pullulan.

2. The lipid nano particle according to claim 1, wherein the content of the ionized lipid is 40 to 65 mol % based on 100 mol % of the lipid components of the lipid nano particle, the content of the phospholipid is 4 to 20 mol % based on 100 mol % of the lipid components of the lipid nano particle, and the content of the sterol is 25 to 50 mol % based on 100 mol % of the lipid components of the lipid nano particle.

3. The lipid nano particle according to claim 1, wherein the content of the ionized lipid is 45 to 60 mol % based on 100 mol % of the lipid components of the lipid nano particle, the content of the phospholipid is 4 to 15 mol % based on 100 mol % of the lipid components of the lipid nano particle, and the content of the sterol is 30 to 45 mol % based on 100 mol % of the lipid components of the lipid nano particle.

4. The lipid nano particle according to claim 1, wherein the hydrophobic group includes a hydrophobic group having a sterol skeleton.

5. The lipid nano particle according to claim 1, wherein the modified polysaccharide has a weight average molecular weight of 5000 to 2,000,000.

6. The lipid nano particle according to claim 1, comprising a drug agent.

7. The lipid nano particle according to claim 6, wherein the drug agent is a nucleic acid.

8. The lipid nano particle according to claim 7, wherein the nucleic acid is at least one member selected from the group consisting of mRNA, immunostimulatory double-stranded RNA, siRNA, miRNA, ribozyme, CpG oligo DNA, antisense oligo DNA, nucleic acid aptamer, decoy, double-stranded DNA for gene expression, and dinucleotide.

9. The lipid nano particle according to claim 7, wherein the nucleic acid is mRNA or CpG oligo DNA.

10. The lipid nano particle according to claim 7, wherein the nucleic acid is mRNA.

11. The lipid nano particle according to claim 7, wherein the nucleic acid is CpG oligo DNA.

12. The lipid nano particle according to claim 1, wherein the ionized lipid is at least one member selected from the group consisting of amino lipids represented by formula (1):

(1)

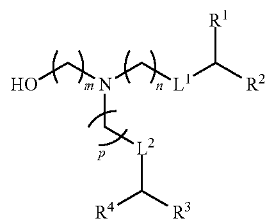

wherein $R^1$ represents an alkyl group, $R^2$ represents an alkyl group, $R^3$ represents an alkyl group, $R^4$ represents an alkyl group or a hydrogen atom, $L^1$ represents —O—C(═O)— or —C(═O)—O—, $L^2$ represents —O—C(═O)— or —C(═O)—O—, m represents an integer of 1 to 8, n represents an integer of 3 to 10, and p represents an integer of 3 to 10;

amino lipids represented by formula (2):

(2)

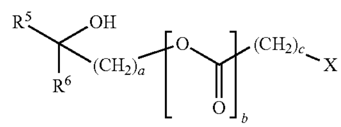

wherein a represents an integer of 3 to 5, b represents 0 or 1, c represents an integer of 0 to 4, $R^5$ and $R^6$ are the same or different and represent an alkyl group or an alkenyl group, and X represents an optionally substituted non-aromatic nitrogen-containing heterocyclic group or an optionally substituted amino group;

and amino lipids represented by formula (3):

(3)

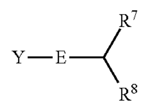

wherein $R^7$ and $R^8$ are the same or different and represent an alkyl group or an alkenyl group, Y represents an optionally substituted non-aromatic nitrogen-containing heterocyclic group or an optionally substituted amino group, and E represents a linker.

13. The lipid nano particle according to claim 1, further comprising a complex lipid that inhibits particle aggregation.

14. The nano lipid particle according to claim 13, wherein the content of the complex lipid is 0 to 2 mol % based on 100 mol % of the lipid components of the lipid nano particle.

15. The nano lipid particle according to claim 13, wherein the complex lipid is a polyethylene glycol-lipid conjugate.

16. The nano lipid particle according to claim 1, wherein the mass average particle size is 10 to 200 nm.

17. A medicine comprising the lipid nano particle according to claim 1.

18. The medicine according to claim 17, which is a therapeutic drug for cancers, immune disorders, central nervous system diseases, etc., an infectious disease vaccine, or a cancer vaccine.

19. The medicine according to claim 17, which is for use in subcutaneous, transvenous, intramuscular, intranasal, or intra-airway administration.

* * * * *